US010172779B2

(12) United States Patent
Hori et al.

(10) Patent No.: US 10,172,779 B2
(45) Date of Patent: Jan. 8, 2019

(54) COPOLYMER HAVING CARBOSILOXANE DENDRIMER STRUCTURE AND COMPOSITION AND COSMETIC CONTAINING THE SAME

(71) Applicant: DOW CORNING TORAY CO., LTD., Tokyo (JP)

(72) Inventors: Seiji Hori, Fukui (JP); Tomohiro Iimura, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 14/422,774

(22) PCT Filed: Aug. 22, 2013

(86) PCT No.: PCT/JP2013/073071
§ 371 (c)(1),
(2) Date: Feb. 20, 2015

(87) PCT Pub. No.: WO2014/030771
PCT Pub. Date: Feb. 27, 2014

(65) Prior Publication Data
US 2015/0216787 A1 Aug. 6, 2015

(30) Foreign Application Priority Data
Aug. 22, 2012 (JP) ................................ 2012-182850

(51) Int. Cl.
| | | |
|---|---|---|
| *A61K 8/81* | (2006.01) | |
| *C08F 220/18* | (2006.01) | |
| *A61K 8/92* | (2006.01) | |
| *A61Q 1/10* | (2006.01) | |
| *A61Q 17/04* | (2006.01) | |
| *A61Q 1/06* | (2006.01) | |
| *A61Q 1/04* | (2006.01) | |
| *C08F 230/08* | (2006.01) | |
| *A61Q 1/02* | (2006.01) | |
| *A61Q 1/08* | (2006.01) | |
| *A61Q 19/00* | (2006.01) | |
| *A61K 8/891* | (2006.01) | |
| *C08G 77/14* | (2006.01) | |

(52) U.S. Cl.
CPC ............ *A61K 8/8152* (2013.01); *A61K 8/891* (2013.01); *A61K 8/92* (2013.01); *A61Q 1/02* (2013.01); *A61Q 1/04* (2013.01); *A61Q 1/06* (2013.01); *A61Q 1/08* (2013.01); *A61Q 1/10* (2013.01); *A61Q 17/04* (2013.01); *A61Q 19/00* (2013.01); *C08F 220/18* (2013.01); *C08F 230/08* (2013.01); *A61K 2800/544* (2013.01); *C08G 77/14* (2013.01)

(58) Field of Classification Search
CPC .... C08F 220/18; C08F 230/08; C08F 220/14; A61K 2800/544; A61K 8/8152; A61K 8/891; C08G 77/14
See application file for complete search history.

(56) References Cited

U.S. PATENT DOCUMENTS

| | | |
|---|---|---|
| 4,980,167 A | 12/1990 | Harashima et al. |
| 5,628,989 A | 5/1997 | Harashima et al. |
| 5,654,362 A | 8/1997 | Schulz, Jr. et al. |
| 5,939,478 A | 8/1999 | Beck et al. |
| 5,981,680 A | 11/1999 | Petroff et al. |
| 6,238,656 B1 | 5/2001 | Morita et al. |
| 6,238,745 B1 | 5/2001 | Morita et al. |
| 6,280,748 B1 | 8/2001 | Morita et al. |
| 6,289,748 B1 * | 9/2001 | Lin .................... G01L 3/105 73/862.331 |
| 6,291,021 B1 | 9/2001 | Morita et al. |
| 6,306,992 B1 | 10/2001 | Yoshitake et al. |
| 6,420,504 B1 | 7/2002 | Yoshitake et al. |
| 6,534,590 B1 | 3/2003 | Aso et al. |
| 6,602,949 B2 | 8/2003 | Furukawa et al. |
| 7,244,439 B2 | 7/2007 | Yago et al. |
| 7,482,419 B2 | 1/2009 | Caprasse et al. |
| 7,488,492 B2 | 2/2009 | Furukawa et al. |
| 7,722,899 B2 | 5/2010 | Ono et al. |
| 8,034,891 B2 | 10/2011 | Okawa |

(Continued)

FOREIGN PATENT DOCUMENTS

| | | |
|---|---|---|
| CN | 101084863 A | 12/2007 |
| CN | 101472979 A | 7/2009 |

(Continued)

OTHER PUBLICATIONS

PCT/JP2013/073071 International Search Report dated Mar. 5, 2014, 3 pages.
English language abstract and machine assisted English translation for JPH08-12524 extracted from http://www4.ipdl.inpit.go.jp/ database on Feb. 17, 2015, 9 pages.
English language abstract and machine assisted English translation for JPH08-12546 extracted from http://www4.ipdl.inpit.go.jp/ database on Feb. 17, 2015, 9 pages.
English language abstract and machine assisted English translation for JPH09-241511 extracted from http://www4.ipdl.inpit.go.jp/ database on Feb. 17, 2015, 8 pages.
English language abstract and machine assisted English translation for JPH10-36219 extracted from http://www4.ipdl.inpit.go.jp/ database on Feb. 17, 2015, 13 pages.

(Continued)

*Primary Examiner* — Anna R Falkowitz
(74) *Attorney, Agent, or Firm* — Warner Norcross & Judd LLP

(57) ABSTRACT

A copolymer in which from 45 to 60% by mass of all monomer units are unsaturated monomers having a specific carbosiloxane dendrimer structure is disclosed, along with a composition, a cosmetic raw material, and a cosmetic containing the copolymer. The copolymer has excellent physical properties, including compatibility with other cosmetic raw materials, e.g. hardly soluble ultraviolet absorbers, and is capable of improving the compounding stability of cosmetics. The copolymer imparts cosmetics with good water resistance, sebum resistance, luster, tactile sensation, and adhesiveness to the hair or skin.

20 Claims, No Drawings

(56) References Cited

U.S. PATENT DOCUMENTS

| | | | |
|---|---|---|---|
| 8,784,787 | B2 | 7/2014 | Tamura et al. |
| 2004/0156809 | A1 | 8/2004 | Ono et al. |
| 2005/0008597 | A1 | 1/2005 | Furukawa et al. |
| 2006/0193803 | A1 | 8/2006 | Farcet |
| 2008/0003195 | A1 | 1/2008 | Arnaud et al. |
| 2008/0269358 | A1 | 10/2008 | Inoue et al. |
| 2010/0036062 | A1 | 2/2010 | Okawa |
| 2011/0104222 | A1 | 5/2011 | Iida et al. |
| 2011/0110995 | A1 | 5/2011 | Hasegawa et al. |
| 2011/0182846 | A1 | 7/2011 | Ikeda et al. |
| 2012/0141162 | A1 | 6/2012 | Mayuzumi et al. |
| 2012/0251605 | A1 | 10/2012 | Iimura et al. |
| 2012/0263662 | A1* | 10/2012 | Iimura .................. A61K 8/891 424/59 |
| 2012/0269747 | A1 | 10/2012 | Iimura et al. |
| 2013/0096206 | A1 | 4/2013 | Iimura et al. |
| 2013/0102686 | A1 | 4/2013 | Tamura et al. |
| 2013/0210930 | A1 | 8/2013 | Souda et al. |
| 2014/0371330 | A1 | 12/2014 | Hayashi et al. |
| 2015/0232601 | A1* | 8/2015 | Furukawa ............. C08F 230/08 514/772.1 |

FOREIGN PATENT DOCUMENTS

| | | | |
|---|---|---|---|
| EP | 0963751 | A2 | 12/1999 |
| EP | 1055674 | A1 | 11/2000 |
| JP | H02-243612 | A | 9/1990 |
| JP | H05237360 | A | 9/1993 |
| JP | H07196946 | A | 8/1995 |
| JP | H08-12524 | A | 1/1996 |
| JP | H08-12545 | A | 1/1996 |
| JP | H08-12546 | A | 1/1996 |
| JP | H09136812 | A | 5/1997 |
| JP | H09171154 | A | 6/1997 |
| JP | H09-241511 | A | 9/1997 |
| JP | 2704730 | B2 | 1/1998 |
| JP | H10-36219 | A | 2/1998 |
| JP | H11-001530 | A | 1/1999 |
| JP | H11-193331 | A | 7/1999 |
| JP | 2000-063225 | A | 2/2000 |
| JP | 2000119139 | A | 4/2000 |
| JP | 2000226551 | A | 8/2000 |
| JP | 2000-281523 | A | 10/2000 |
| JP | 2003-226611 | A | 8/2003 |
| JP | 4009382 | B2 | 9/2007 |
| JP | 2007-532754 | A | 11/2007 |
| JP | 201018612 | A | 1/2010 |
| JP | 2010-143833 | A | 7/2010 |
| JP | 2011-016733 | A | 1/2011 |
| JP | WO 2011/078407 | * | 6/2011 ............... A61K 8/81 |
| JP | 2011-148784 | A | 8/2011 |
| JP | 2011-149017 | A | 8/2011 |
| JP | 2011-246704 | A | 12/2011 |
| JP | 2011-246705 | A | 12/2011 |
| JP | 2011-246706 | A | 12/2011 |
| JP | 2012118510 | A | 6/2012 |
| JP | 2012136677 | A | 7/2012 |
| JP | 2013151657 | A | 8/2013 |
| WO | WO021000356 | A1 | 12/2002 |
| WO | WO2006106728 | A1 | 10/2006 |
| WO | WO2008072716 | A1 | 6/2008 |
| WO | WO2009022621 | A1 | 2/2009 |
| WO | WO2009142047 | A1 | 11/2009 |
| WO | WO2010026538 | A1 | 3/2010 |
| WO | WO2011049246 | A1 | 4/2011 |
| WO | WO2011049248 | A1 | 4/2011 |
| WO | WO2011078407 | A1 | 6/2011 |
| WO | WO2011078408 | A1 | 6/2011 |
| WO | WO2012091161 | A2 | 7/2012 |
| WO | WO2012091178 | A1 | 7/2012 |

OTHER PUBLICATIONS

English language abstract and machine assisted English translation for JPH11-001530 extracted from http://www4.ipdl.inpit.go.jp/ database on Feb. 20, 2015, 15 pages.

English language abstract and machine assisted English translation for JP2010-143833 extracted from http://www4.ipdl.inpit.go.jp/ database on Feb. 18, 2015, 18 pages.

English language abstract and machine assisted English translation for JP2011-016733 extracted from http://www4.ipdl.inpit.go.jp/ database on Feb. 18, 2015, 21 pages.

English language abstract for JP2704730 extracted from espacenet. com on Feb. 23, 2015, 2 pages.

Machine assisted English translation for JP2704730 extracted from http://www4.ipdl.inpit.go.jp/ database on Feb. 19, 2015, 8 pages.

English language abstract and machine translation for JP2000119139 (A) extracted from http://worldwide.espacenet.com database on Oct. 13, 2016, 14 pages.

PCT/JP2010/073861 International Search Report dated May 26, 2011, 3 pages.

English language abstract and machine translation for JPH09171154 (A) extracted from http://worldwide.espacenet.com database on Oct. 3, 2016, 22 pages.

Shin-Etsu Technical Data Sheet for KF-9909 (Assessed on Sep. 30, 2016), pp. 1-2, https://www.shinetsusilicone-global.com/products/personalcare/pdf/KF/KF-9909.pdf.

"Clearco Product Information for decamethylcyclopentasiloxane" http://www.clearcoproducts.com/pdf/cosmetic/NP-Cyclo-2245%20(D5).pdf, assessed on Sep. 30, 2016, 1 page.

PCT/JP2010/073862, International Search Report dated May 26, 2011, 3 pages.

PCT/JP2013/073069, International Search Report dated Mar. 5, 2014, 3 pages.

English language abstract and machine translation for JPH09136812 (A) extracted from http://worldwide.espacenet.com database on Oct. 3, 2016, 14 pages.

English language abstract and machine translation for JP2000119139 (A) extracted from http://worldwide.espacenet.com database on Oct. 3, 2016, 14 pages.

English language abstract and machine translation for JPH05237360 (A) extracted from http://worldwide.espacenet.com database on Oct. 3, 2016, 18 pages.

English language abstract and machine translation for JPH07196946 (A) extracted from http://worldwide.espacenet.com database on Oct. 3, 2016, 16 pages.

English language abstract for WO2006106728 (A1) extracted from http://worldwide.espacenet.com database on Oct. 3, 2016, 2 pages.

* cited by examiner

COPOLYMER HAVING CARBOSILOXANE DENDRIMER STRUCTURE AND COMPOSITION AND COSMETIC CONTAINING THE SAME

CROSS-REFERENCE TO RELATED APPLICATIONS

This application is the National Stage of International Patent Application No. PCT/JP2013/073071, filed on Aug. 22, 2013, which claims priority to and all advantages of Japanese Patent Application No. 2012-182850, filed on Aug. 22, 2012, the content of which is hereby incorporated by reference.

TECHNICAL FIELD

The present invention relates to a cosmetic. More particularly, the present invention relates to a copolymer having a specific carbosiloxane dendrimer structure and a composition and cosmetic containing the same.

BACKGROUND ART

The idea of compounding a radical polymerizable group-containing organopolysiloxane and a radical polymerizable monomer as a film former for a cosmetic has long been known. For example, it is proposed in Japanese Patent No. 2704730 to compound a vinyl polymer obtained by copolymerizing a dimethylpolysiloxane containing a radical polymerizable group at one terminal and various alkyl acrylates with a cosmetic as a film former. However, although these vinyl polymers impart water repellency and sliding properties to a cosmetic, the polymers are subjected to the grafting of straight-chain silicone, so the compatibility with other cosmetic raw materials is low, and the compounding stability of the cosmetic is poor. This leads to the drawback that a film formed by the polymers will not have sufficient sebum resistance or adhesiveness to the hair or skin.

In order to solve these problems, cosmetic raw materials containing as a primary ingredient a vinyl copolymer having a carbosiloxane dendrimer structure or a vinyl polymer having both a carbosiloxane dendrimer structure and fluorinated organic groups have been proposed (see Japanese Unexamined Patent Application Publication No. 2000-63225 and Japanese Unexamined Patent Application Publication No. 2003-226611). However, although such a vinyl polymer has the feature that it can be used to prepare a cosmetic having very high water resistance, sebum resistance, and durability in a system in which the amount of a UV absorber that is used is small, it has become clear that when a large amount of a UV absorber is added in order to give the vinyl polymer a protective capability over a wide ultraviolet range, there is a problem with compounding stability in that the compatibility between the added ultraviolet absorber and the copolymer is low and the copolymer precipitates. In particular, many cosmetics containing hardly soluble ultraviolet absorbers have been proposed in recent years in order to maintain the ultraviolet protective capability for a long period of time over a wide range, and there has been a demand to solve the problem that copolymers having carbosiloxane dendrimers precipitate in systems with high ultraviolet absorber content. On the other hand, in order to solve these problems, inventions which solve the aforementioned problems by adding a polar oil or the like having specific solubility parameters have been proposed in Japanese Unexamined Patent Application Publication No. 2011-016733 or Japanese Unexamined Patent Application Publication No. 2010-143833. However, when a polar oil is compounded with a cosmetic in order to ensure the compounding stability, there is a problem in that the water resistance and sebum resistance originating from the carbosiloxane dendrimer structure are diminished, and there has been a demand for a solution to this problem.

On the other hand, in Japanese Unexamined Patent Application Publication No. 2011-149017 and Japanese Unexamined Patent Application Publication No. 2011-148784, the inventors of the invention of the present application proposed a cosmetic raw material and a powder treatment agent using a polymer having a specific carbosiloxane dendrimer structure. However, although these polymers demonstrated excellent properties such as dispersion stability of the powder and compounding stability in cosmetics, there remained room for further improvement from the perspectives of the compatibility between hardly soluble ultraviolet absorbers and the copolymer, water resistance, and sebum resistance.

CITATION LIST

Patent Literature

Patent Document 1: Japanese Patent No. 2704730
Patent Document 2: Japanese Unexamined Patent Application Publication No. 2000-063225A
Patent Document 3: Japanese Unexamined Patent Application Publication No. 2003-226611A
Patent Document 4: Japanese Unexamined Patent Application Publication No. 2010-143833A
Patent Document 5: Japanese Unexamined Patent Application Publication No. 2011-016733A
Patent Document 6: Japanese Unexamined Patent Application Publication No. 2011-148784A
Patent Document 7: Japanese Unexamined Patent Application Publication No. 2011-149017A

SUMMARY OF INVENTION

Technical Problem

The present invention was conceived in light of the current state of the prior art, and the object of the present invention is to provide a cosmetic raw material having good compatibility with other cosmetic raw materials—hardly soluble ultraviolet absorbers, in particular—and capable of improving the compounding stability of a cosmetic and imparting the cosmetic with good water resistance, sebum resistance, luster, tactile sensation, and adhesiveness to the hair or skin, and a cosmetic with excellent surface protective characteristics, appearance, and feel of use formed by adding this cosmetic raw material.

Solution to Problem

As a result of conducting dedicated research, the present inventors discovered that a copolymer having unsaturated monomers having a specific carbosiloxane dendrimer structure within a range of from 45 to 60% by mass of all monomer units demonstrates excellent compatibility with ultraviolet absorbers and that a cosmetic containing this specific copolymer can provide a cosmetic with excellent water resistance, sebum resistance, and compounding stability. Further, it became clear that using this specific amount of unsaturated monomers having a carbosiloxane dendrimer structure not only improves the water resistance and sebum resistance of the cosmetic, but also enhances the adherence of the copolymer of the present invention to the skin.

The specific object of the present invention is achieved by a copolymer in which at least from 45 to 60% by mass of all monomer units are unsaturated monomers having a carbosiloxane dendrimer structure represented by the following formula (1):

[Formula 1]

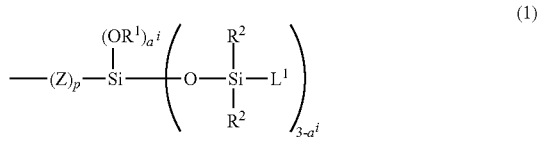
(1)

wherein,
Z is a divalent organic group;
p is 0 or 1;
$R^1$ and $R^2$ each independently represent a group selected from the group consisting of alkyl groups, aryl groups, and aralkyl groups, having 1 to 10 carbon atoms; and
$L^1$ is a silylalkyl group, in the case of i=1, represented by the following formula (2):

[Formula 2]

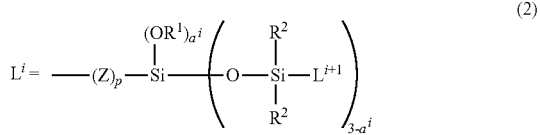
(2)

wherein,
Z and p are the same as defined above;
$R^1$ and $R^2$ are the same as defined above;
i is an integer ranging from 1 to 10 indicating a total number of generations of the silylalkyl group;
$L^{i+1}$ is a group selected from the group consisting of a hydrogen atom, an alkyl group having from 1 to 10 carbon atoms, an aryl group, an aralkyl group, and the silylalkyl group, $L^{i+1}$ being a hydrogen atom, an alkyl group having from 1 to 10 carbon atoms, an aryl group, or an aralkyl group when i=c (c is an integer from 1 to 10 representing hierarchies of the silylalkyl group) and being the silylalkyl group when i<c, and
$a^i$ is an integer from 0 to 3)].

It is preferable that (A) the unsaturated monomers having a carbosiloxane dendrimer structure have groups selected from the group consisting of an acryl group or methacryl group-containing organic group represented by the general formula:

[Formula 3]

(in the formula, $R^4$ is a hydrogen atom or a methyl group; and $R^5$ is an alkylene group having 1 to 10 carbon atoms), an acryl or methacryl group-containing organic group represented by the following general formula:

[Formula 4]

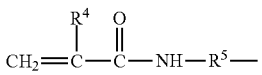

(in the formula, $R^4$ and $R^5$ have the same meaning as defined above), and an alkenylaryl group-containing organic group, or alkenyl group having 2 to 10 carbon atoms as represented by the following general formula:

[Formula 5]

(in the formula, $R^6$ is a hydrogen atom or a methyl group, $R^7$ is an alkyl group having from 1 to 10 carbon atoms, $R^8$ is an alkylene group having from 1 to 10 carbon atoms, b is an integer from 0 to 4, and c is 0 or 1), and an alkenyl group having from 2 to 10 carbon atoms.

Further, the copolymer of the present invention may be obtained by copolymerizing at least (A) the unsaturated monomers having a carbosiloxane dendrimer structure and (B) at least one type of unsaturated monomer not having long-chain alkyl groups of from 14 to 22 carbon atoms in the molecule. In particular, the copolymer is preferably obtained by copolymerizing (A) the unsaturated monomers having a carbosiloxane dendrimer structure and (B) the at least one type of unsaturated monomer not having long-chain alkyl groups of from 14 to 22 carbon atoms in the molecule within a mass ratio range satisfying a relation in which [mass of component (A)/mass of all monomers]:[mass of component (B)/mass of all monomers] is [0.45 to 0.55:0.55 to 0.45], and it is particularly preferable for the component (B) to be (B1) an acrylic acid ester-based monomer or a methacrylic acid ester-based monomer having from 4 to 13 carbon atoms. Further, the copolymer of the present invention is most preferably designed so that the type of the component (B) and the amount of the reaction are adjusted within the ranges described above and so that the calculated glass transition point (Tg) is from 40 to 90 degrees.

Finally, the object of the present invention is achieved by a cosmetic containing the copolymer described above. That is, the copolymer described above can be very suitably used as a film forming component of a cosmetic. Further, the copolymer of the present invention may also be used as a surface treating agent of various substrates since the copolymer has film formability.

Further, the copolymer of the present invention can be suitably compounded with a cosmetic in the form of a copolymer composition which is dispersed or uniformly dissolved in (C) an oil agent. The cosmetic of the present invention may contain an oil agent derived from the copolymer composition described above and may also be a cosmetic to which a desired oil agent is added separately depending on the type and formula of the cosmetic. In addition, the (C) oil agent is a liquid at a temperature of from 5 to 100° C. and is preferably at least one type selected from silicone oils, hydrocarbon oils, and fatty acid ester oils.

In particular, the oil agent is preferably a silicone oil, and this silicone oil is preferably a hydrophobic silicone oil with a viscosity of from 0.65 to 100,000 mm²/s at 25° C.

The silicone oil described above may be an organopolysiloxane represented by one of the following general formulas (3), (4), or (5):

[Formula 6]

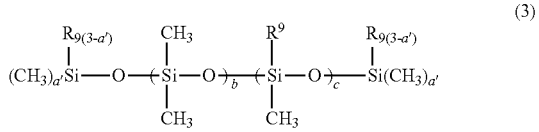

(3)

wherein,
$R^9$ is a hydrogen atom, hydroxyl group, or a group selected from monovalent unsubstituted or fluorine- or amino-substituted alkyl groups, aryl groups, or alkoxy groups, having 1 to 30 carbon atoms, and groups represented by $(CH_3)_3SiO\{(CH_3)_2SiO\}_I Si(CH_3)_2 CH_2 CH_2$— (where I is an integer ranging from 0 to 1,000);
a' is an integer from 0 to 3;
b is an integer from 0 to 1,000; and
c' is an integer from 0 to 1,000, where $1 \leq b+c \leq 2,000$.

[Formula 7]

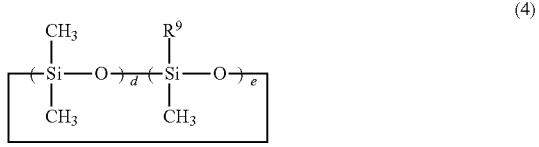

(4)

wherein,
$R^9$ is the same as described above;
d is an integer from 0 to 8; and
e is an integer from 0 to 8, where $3 \leq d+e \leq 8$.

[Formula 8]

(5)

wherein,
$R^9$ is the same as described above;
f is an integer from 1 to 4; and
g is an integer from 0 to 500.

The cosmetic of the present invention may further contain (D) a powder or colorant. This powder may be at least one type selected from the group consisting of inorganic pigment powders, organic pigment powders, and resin powders with an average particle diameter within the range of from 1 nm to 20 μm. At least part of the powder or colorant may be subjected to water repellency treatment.

The cosmetic of the present invention may further contain (E) a surfactant. The surfactant may be at least one type selected from the group consisting of anionic surfactants, cationic surfactants, nonionic surfactants, and amphoteric surfactants.

The cosmetic of the present invention may further contain at least one type selected from the group consisting of (F) an oil-soluble gelling agent, (G) an organically modified clay mineral, (H) a silicone resin, (I) a silicone rubber, (J) a silicone elastomer, (K) an organically modified silicone, (L) an ultraviolet ray protective component, and (M) a water-soluble polymer.

The cosmetic of the present invention may be, in particular, a skin care product, a hair product, an antiperspirant product, a deodorant product, a makeup product, or an ultraviolet ray protective product.

Advantageous Effects of Invention

In the copolymer of the present invention, a specific amount of a dendrimer-type silicone, which is not straight-chained but is branched to a high degree, is grafted to the main chain, and the copolymer has good compatibility with various other cosmetic raw materials such as ultraviolet absorbers, in particular, so the copolymer has excellent compounding stability in a system to which an ultraviolet absorber is added. Moreover, since the copolymer of the present invention imparts good water resistance, sebum resistance, luster, and tactile sensation and also demonstrates adherence to the skin, the copolymer has the advantage that it can impart a cosmetic with adhesiveness to the hair or skin in addition to the favorable characteristics described above.

The cosmetic of the present invention contains the copolymer described above, which yields excellent surface protective characteristics such as water resistance, sebum resistance, luster, tactile sensation, adherence to the hair and skin, and adhesiveness as well as appearance and feel of use.

DETAILED DESCRIPTION OF THE INVENTION

<Copolymer>

The copolymer of the present invention is a copolymer in which at least from 45 to 60% by mass of all monomers are unsaturated monomers having a carbosiloxane dendrimer structure represented by the following formula (1):

[Formula 9]

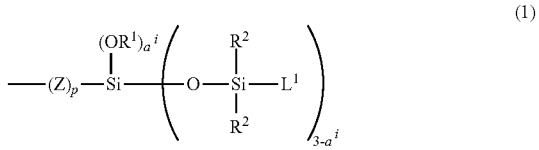

(1)

wherein,
Z is a divalent organic group;
p is 0 or 1;
$R^1$ and $R^2$ each independently represent a group selected from the group consisting of alkyl groups, aryl groups, and aralkyl groups, having 1 to 10 carbon atoms; and
$L^1$ is a silylalkyl group, in the case of i=1, represented by the following formula (2):

[Formula 10]

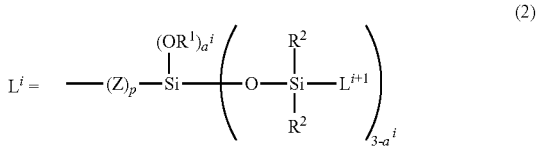

(2)

wherein,
Z and p are the same as defined above;
$R^1$ and $R^2$ are the same as defined above;
i is an integer ranging from 1 to 10 indicating a total number of generations of the silylalkyl group, and i is preferably 1 to 5, more preferably 1 to 3, and further preferably 1 or 2;

$L^{i+1}$ is a group selected from the group consisting of a hydrogen atom, an alkyl group having from 1 to 10 carbon atoms, an aryl group, an aralkyl group, and the silylalkyl group when i=c (c is an integer from 1 to 10 representing hierarchies of the silylalkyl group and is preferably from 1 to 5, more preferably from 1 to 3, and even more preferably 1 or 2), and the silylalkyl group, $L^{i+1}$ being a hydrogen atom, an alkyl group having from 1 to 10 carbon atoms, an aryl group, or an aralkyl group and being the silylalkyl group when i<c, and $a^i$ is an integer from 0 to 3 and is preferably from 0 to 2, more preferably 0 or 1, and even more preferably 0)], and the copolymer contains these unsaturated monomers in the main chain.

Here, the copolymer of the present invention is preferably a copolymer of (A) unsaturated monomers having a carbosiloxane dendrimer structure and (B) unsaturated monomers not having long-chain alkyl groups of from 14 to 22 carbon atoms. The ratio (mass ratio) of unsaturated monomers having a carbosiloxane dendrimer structure and unsaturated monomers not having long-chain alkyl groups of from 14 to 22 carbon atoms is preferably within the range of from (A):(B)=0.45 to 0.6:0.55 to 0.4 and more preferably from 0.45 to 0.55:0.55 to 0.45.

When the amount of the component (A) used in copolymerization is less than the lower limit described above, the compatibility with hardly soluble ultraviolet absorbers and the like is insufficient, and in a system containing a large amount of an ultraviolet absorber, there is a problem in that a copolymer having a carbosiloxane dendrimer structure precipitates, which results in poor compounding stability. Further, with regard to the film properties, even if the glass transition point of the copolymer is adjusted by the component (B) and the film strength is adjusted to yield desired physical properties, the hard texture remains, and when this is applied to the skin or hair as a cosmetic, there is a problem in that there is a strong coating feeling. In addition, the sebum resistance, tactile sensation, or the like may be diminished.

On the other hand, when the amount of the component (A) exceeds the upper limit described above, the compounding stability is improved, but the molecular weight of the copolymer may not improve to the target molecular weight due to the steric hindrance of the carbosiloxane dendrimer structure, which makes the synthesis of the copolymer itself difficult.

In formula (1), the divalent organic group is not particularly limited, and examples include substituted or unsubstituted and straight-chain or branched divalent hydrocarbon groups having from 1 to 30 carbon atoms. Examples of the substituted or unsubstituted, and linear or branched divalent hydrocarbon group having 1 to 30 carbon atoms include: linear or branched alkylene groups having 1 to 30 carbon atoms such as the methylene group, dimethylene group, trimethylene group, tetramethylene group, pentamethylene group, hexamethylene group, heptamethylene group, octamethylene group, or the like; alkenylene groups having 2 to 30 carbon atoms such as the vinylene group, allylene group, butenylene group, hexenylene group, octenylene group, or the like; arylene groups having 6 to 30 carbon atoms such as the phenylene group, diphenylene group, or the like; alkylenearylene groups having 7 to 30 carbon atoms such as the dimethylenephenylene group or the like; and substituted groups thereof in which hydrogen atoms bonded to carbon atoms of the groups are at least partially substituted by a halogen atom such as a fluorine atom or the like, or an organic group containing the carbinol group, epoxy group, glycidyl group, acyl group, carboxyl group, amino group, methacryl group, mercapto group, amide group, oxyalkylene group, or the like. The divalent hydrocarbon group is preferably an unsubstituted divalent saturated hydrocarbon group having 1 to 30 carbon atoms, more preferably is a linear or branched alkylene group having 1 to 6 carbon atoms, and particular preferably is a dimethylene group.

For example, the divalent organic group may be a group selected from the following groups:

—$R^3$—

—$R^3$—CO—

—$R^3$—COO—$R^{3'}$—

—CO—$R^3$—

—$R^3$—COO—$R^{3'}$—

—$R^3$—CONH—$R^{3'}$—

—$R^3$-$R^{3'}$—  [Formula 11]

wherein, $R^3$ is the substituted or unsubstituted, and linear or branched divalent hydrocarbon group having 1 to 30 carbon atoms, which may have a substituent as described above; and $R^{3'}$ is a group selected from the following groups:

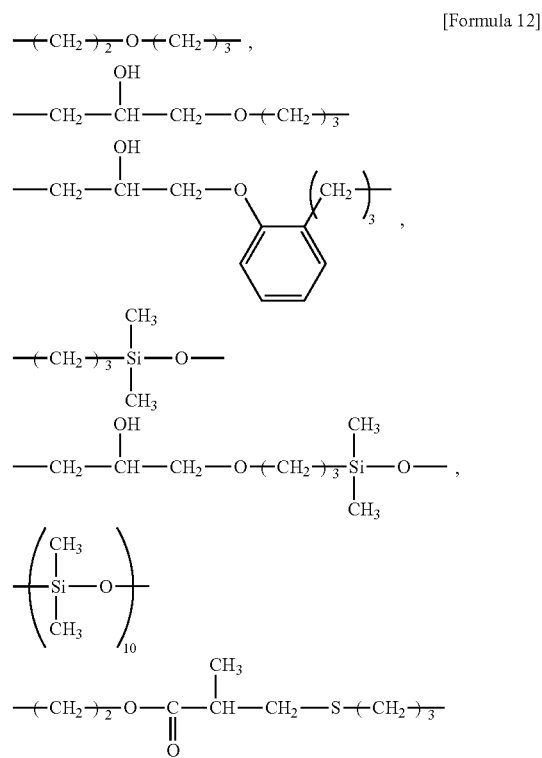

[Formula 12]

A divalent organic group represented by the general formula —$R^3$— or —$R^3$-$R^{3'}$—, which can be introduced by a reaction between a silicon-bonded hydrogen atoms and an alkenyl group, is preferred. In the same manner as described above, a divalent organic group represented by the general formula —$R^3$—COO—$R^{3'}$— or —$R^3$—COO—$R^{3'}$—, which can be introduced by a reaction between a silicon-bonded hydrogen atom and an unsaturated carboxylic acid functional group, is also preferred.

In particular, Z is preferably a linear or branched alkylene group having 1 to 30 carbon atoms, and particularly preferably is the dimethylene group (ethylene group).

Examples of alkyl groups, aryl groups, or aralkyl groups having 1 to 10 carbon atoms include: linear or branched alkyl groups having 1 to 30 carbon atoms such as the methyl group, ethyl group, propyl group, butyl group, pentyl group, hexyl group, heptyl group, octyl group, and the like; cycloalkyl groups having 3 to 10 carbon atoms such as the cyclopentyl group, cyclohexyl group, and the like; aryl groups having 6 to 10 carbon atoms such as the phenyl group, tolyl group, xylyl group, and the like; aralkyl groups having 7 to 10 carbon atoms such as the benzyl group and the like; and substituted groups thereof in which hydrogen atoms bonded to carbon atoms of the groups are at least partially substituted by a halogen atom such as a fluorine atom and the like, or an organic group containing the carbinol group, epoxy group, glycidyl group, acyl group, carboxyl group, amino group, methacryl group, mercapto group, amide group, oxyalkylene group, and the like. The alkyl groups, aryl groups or aralkyl groups are preferably unsubstituted alkyl groups, aryl groups or aralkyl groups having from 1 to 10 carbon atoms, more preferably unsubstituted alkyl groups or aryl groups having from 1 to 6 carbon atoms, and even more preferably a methyl group, ethyl group, or phenyl group.

The carbosiloxane dendrimer structure is a chemical structure radially and highly branched from one silicon atom. The "i" specifying the total number of generations of the silylalkyl group indicates the degree of branching. For example, in the case in which the total number of generations i is 1 and $L^{i+1}$ is, for example, a methyl group, the carbosiloxane dendrimer structure means the following structure:

[Formula 13]

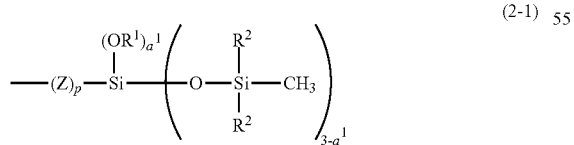

(2-1)

in the formula, Z, p, $R^1$, and $R^2$ are the same as defined above; and $a^1$ is an integer ranging from 0 to 3.

In the same manner as described above, in the case in which the number of generations i is 2 and $L^{i+1}$ is, for example, a methyl group, the carbosiloxane dendrimer structure means the following structure (where p=1):

[Formula 14]

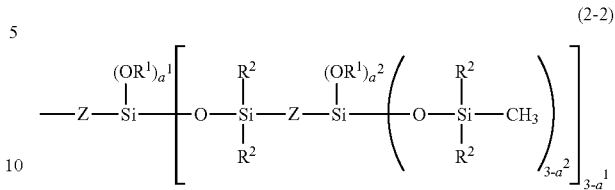

(2-2)

in the formula, Z, $R^1$, and $R^2$ are the same as defined above; and $a^1$ and $a^2$ are integers ranging from 0 to 3.

Further, in the case in which the number of generations i is 3 and $L^{i+1}$ is, for example, a methyl group, the carbosiloxane dendrimer structure means the following structure (where p=1):

[Formula 15]

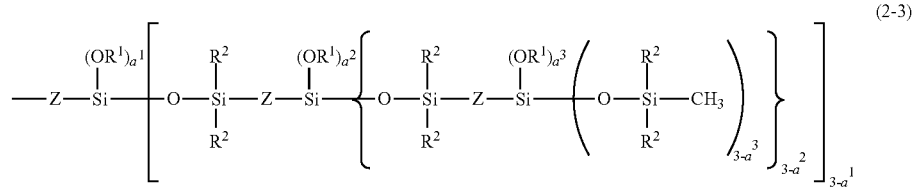

(2-3)

in the formula, Z, $R^1$, and $R^2$ are the same as defined above; and $a^1$, $a^2$, and $a^3$ are integers ranging from 0 to 3.

The following structures are particularly preferred as the carbosiloxane dendrimer structure:

[Formula 16]

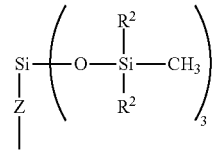

in the formula, Z and $R^2$ are the same as defined above,

[Formula 17]

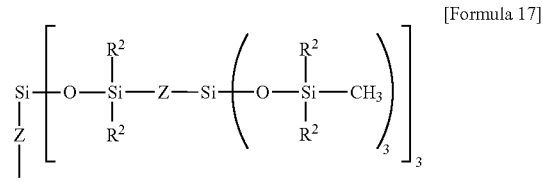

in the formula, Z and $R^2$ are the same as defined above,

The silylalkyl group having the carbosiloxane dendrimer structure has a structure in which the carbosiloxane units are extended in the form of a dendrimer. For this reason, the silylalkyl group is a functional group exhibiting increased water repellency (increased water resistance) in comparison to linear or simply branched polysiloxane units. Additionally, the silylalkyl group having a carbosiloxane dendrimer structure is chemically stable, and for this reason, the silylalkyl group is a functional group providing advantageous properties such as usability in combination with a wide range of raw materials for use in cosmetic compositions.

The (A) unsaturated monomer having the carbosiloxane dendrimer structure, for example, is represented by the following formula (1'):

[Formula 18]

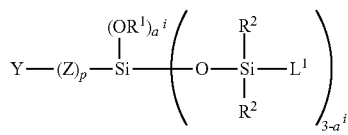

(1')

wherein,
Y is an unsaturation-containing group capable of radical polymerization; and
Z, p, $R^1$, $R^2$, $L^1$, and $a^i$ are the same as described above).

The unsaturation-containing group is not particularly restricted as long as the unsaturation-containing group has a radically polymerizable unsaturation. The unsaturation-containing group is exemplified by the vinyl group, allyl group, (meth)acryl group, or the like.

It is preferable that (A) the unsaturated monomers having a carbosiloxane dendrimer structure have groups selected from the group consisting of an acryl group or methacryl group-containing organic group represented by the general formula:

[Formula 19]

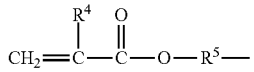

(in the formula, $R^4$ is a hydrogen atom or a methyl group; and $R^5$ is an alkylene group having 1 to 10 carbon atoms), an acryl or methacryl group-containing organic group represented by the following general formula:

[Formula 20]

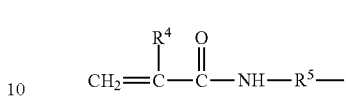

(in the formula, $R^4$ and $R^5$ have the same meaning as defined above), and an alkenylaryl group-containing organic group, or alkenyl group having 2 to 10 carbon atoms as represented by the following general formula:

[Formula 21]

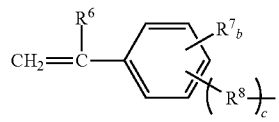

(in the formula, $R^6$ is a hydrogen atom or a methyl group; $R^7$ is an alkyl group having 1 to 10 carbon atoms; $R^8$ is an alkylene group having 1 to 10 carbon atoms; b is an integer ranging from 0 to 4, and c is either 0 or 1).

The (A) unsaturated monomer having the carbosiloxane dendrimer structure is exemplified by the following formulae.

[Formula 22]

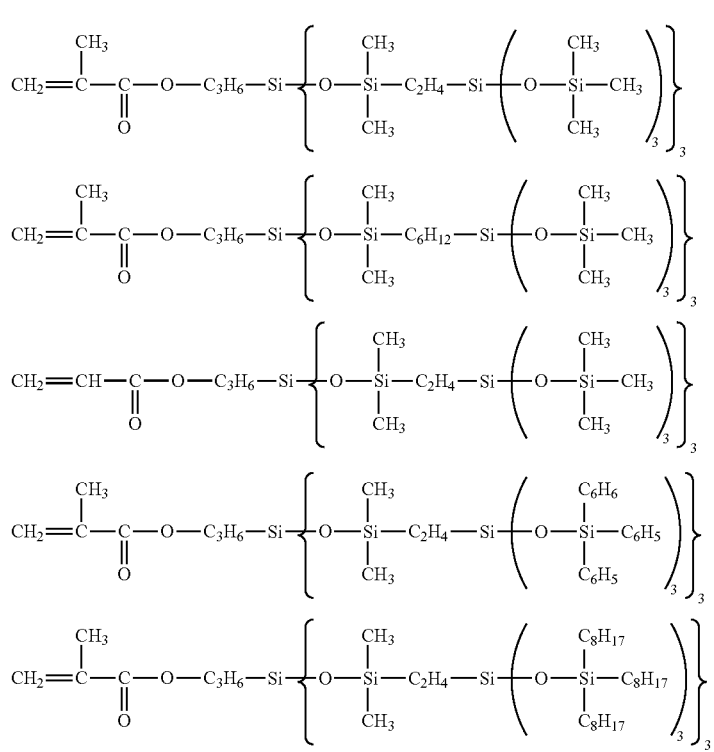

-continued

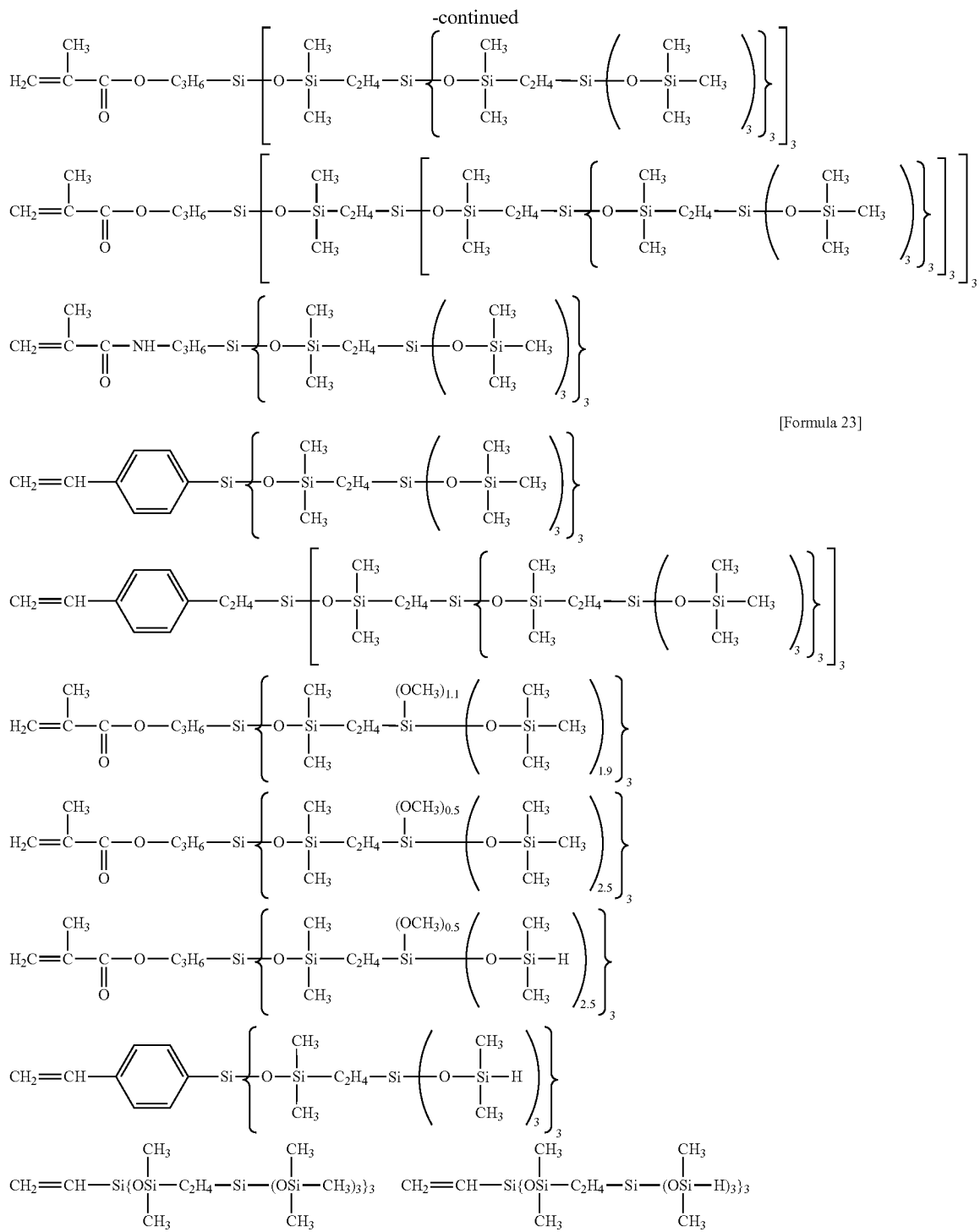

[Formula 23]

The (A) unsaturated monomer having the carbosiloxane dendrimer structure can be produced in accordance with, for example, a method for producing a branched siloxane/silalkylene copolymer described in Japanese Unexamined Patent Application Publication No. H11-001530 (Japanese Patent Application No. H09-171154).

The (B) unsaturated monomer not having long-chain alkyl groups of from 14 to 22 carbon atoms is a component to be grafted to the main chain of the copolymer of the present invention in addition to the silylalkyl group having a carbosiloxane dendrimer structure in order to adjust the copolymer to the desired film properties. Examples of radically polymerizable unsaturated bond-containing groups include monovalent hydrocarbon groups having carbon-carbon double bonds at the molecular chain terminals as unsaturated bonds and groups derived from monovalent unsaturated carboxylic acid. Examples include vinyl groups, allyl groups, (meth)acryl groups, and (meth)acryloxy groups. In the present invention, these unsaturated monomers serving as these components (B) may be a mixture of two or more types, and a molecular design in which heterogeneous functional groups are grafted to the main chain may be implemented with the objective of imparting functionality to the copolymer. That is, in order to obtain the copolymer of the present invention, it is possible and preferable to use two or more types of the components (B). From the standpoint of characteristics such as the ease of procuring raw materials, the compatibility between the resulting copolymer and other cosmetic raw materials, the compounding stability with cosmetics, water resistance, and sebum resistance, the component (B) is preferably (B1) an acrylic acid ester monomer or a methacrylic acid ester monomer having from 4 to 13 carbon atoms. In particular, an acrylic acid ester or methacrylic acid ester having from 4 to 13 carbon atoms—more preferably from 4 to 10 carbon atoms—is preferable. On the other hand, when an unsaturated monomer having long-chain alkyl groups of 14 or more carbon atoms is used, the compatibility with other cosmetic raw materials and the compounding stability with the cosmetic may be diminished, even when the component (A) is used.

Examples of (B) the unsaturated monomer not having long-chain alkyl groups of from 14 to 22 carbon atoms include lower alkyl acrylates or methacrylates such as methyl acrylate, methyl methacrylate, ethyl acrylate, ethyl methacrylate, n-propyl acrylate, n-propyl methacrylate, isopropyl acrylate, and isopropyl methacrylate; glycidyl acrylate and glycidyl methacrylate; acrylic acid esters or methacrylic acid esters having up to 13 carbon atoms such as n-butyl acrylate, n-butyl methacrylate, isobutyl acrylate, isobutyl methacrylate, tert-butyl acrylate, tert-butyl methacrylate, n-hexyl acrylate, n-hexyl methacrylate, n-hexyl acrylate, n-hexyl methacrylate, cyclohexyl acrylate, cyclohexyl methacrylate, 2-ethylhexyl acrylate, 2-ethylhexyl methacrylate, octyl acrylate, octyl methacrylate, lauryl acrylate, and lauryl methacrylate; lower fatty acid vinyl esters such as vinyl acetate and vinyl propionate; higher fatty acid esters having up to 13 carbon atoms such as vinyl butyrate, vinyl caproate, vinyl 2-ethylhexanoate, and vinyl laurate; aromatic vinyl monomers such as styrene, vinyl toluene, benzyl acrylate, benzyl methacrylate, phenoxyethyl acrylate, phenoxyethyl methacrylate, and vinyl pyrrolidone; amino group-containing vinyl monomers such as dimethylaminoethyl acrylate, dimethylaminoethyl methacrylate, diethylaminoethyl acrylate, and diethylaminoethyl methacrylate; amide group-containing vinyl monomers such as acrylamide, methacrylamide, N-methylol acrylamide, N-methylol methacrylamide, N-methylol acrylamide, N-methylol methacrylamide, N-methoxymethyl acrylamide, N-methoxymethyl methacrylamide, isobutoxymethoxy acrylamide, isobutoxymethoxy methacrylamide, N,N-dimethylacrylamide, and N,N-dimethylmethacrylamide; carboxylic acid-containing vinyl monomers such as acrylic acid, methacrylic acid, itaconic acid, crotonic acid, fumaric acid, and maleic acid; ether bond-containing vinyl monomers such as tetrahydrofurfuryl acrylate, tetrahydrofurfuryl methacrylate, butoxyethyl acrylate, butoxyethyl methacrylate, cetyl vinyl ether, and 2-ethylhexyl vinyl ether; unsaturated group-containing silicone compounds such as acryloxypropyl trimethoxysilane, methacryloxypropyl trimethoxysilane, polydimethylsiloxanes containing an acryl group or a methacryl group at one terminal, and polydimethylsiloxanes containing an alkenylaryl group at one terminal; butadiene; vinyl chloride; vinylidene chloride; acrylonitrile and methacrylonitrile; dibutyl fumarate; maleic anhydride; dodecyl succinic anhydride; acryl glycidyl ether, methacryl glycidyl ether, 3,4-epoxycyclohexylmethyl acrylate, and 3,4-epoxycyclohexylmethyl methacrylate; radically polymerizable unsaturated monomers having alkali metal salts, ammonium salts, organic amine salts, or sulfonic acid salts such as styrene sulfonate of radically polymerizable unsaturated carboxylic acids such as acrylic acid, methacrylic acid, itaconic acid, crotonic acid, fumaric acid, and maleic acid, and alkali metal salts, ammonium salts, and organic amine salts thereof; and methacrylic acid esters of alcohols having quaternary ammonium salts derived from acrylic acids or methacrylic acids such as 2-hydroxy-3-methacryloxypropyl trimethyl ammonium chloride and ternary amine groups such as methacrylic acid diethylamine ester, and quaternary ammonium salts thereof In addition, polyfunctional vinyl monomers may also be used as some or all of the components (B), and examples include trimethylolpropane triacrylate, trimethylolpropane trimethacrylate, pentaerythritol triacrylate, pentaerythritol trimethacrylate, ethylene glycol diacrylate, ethylene glycol dimethacrylate, tetraethylene glycol diacrylate, tetraethylene glycol dimethacrylate, polyethylene glycol diacrylate, polyethylene glycol dimethacrylate, 1,4-butanediol diacrylate, 1,4-butanediol dimethacrylate, 1,6-hexanediol diacrylate, 1,6-hexanediol dimethacrylate, neopentyl glycol diacrylate, neopentyl glycol dimethacrylate, trimethylolpropane trioxyethylacrylate, trimethylolpropane trioxyethylmethacrylate, tris(2-hydroxyethyl)isocyanurate diacrylate, tris(2-hydroxyethyl)isocyanurate dimethacrylate, tris(2-hydroxyethyl)isocyanurate triacrylate, tris(2-hydroxyethyl)isocyanurate trimethacrylate, and unsaturated group-containing silicone compounds such as polydimethylsiloxanes having both molecular terminals capped with alkenylaryl groups.

Further, a vinyl monomer containing a fluorinated organic group and not having long-chain alkyl groups of from 14 to 22 carbon atoms may be used. The vinyl monomer containing a fluorinated organic group is preferably represented by the general formula: $CH_2=CR^{15}COOR^f$. In the formula, $R^{15}$ is a hydrogen atom or a methyl group, and $R^f$ is a fluorinated organic group. Examples include a fluoroalkyl group or a fluoroalkyloxyfluoroalkylene group, as described above. Specific examples of such a component (B) include compounds represented by the following formulas. In the following formulae, z is an integer ranging from 1 to 4.
$CH_2=CCH_3COO-CF_3$, $CH_2=CCH_3COO-C_2F_5$, $CH_2=CCH_3COO-nC_3F_7$, $CH_2=CCH_3COO-CF(CF_3)_2$, $CH_2=CCH_3COO-nC_4F_9$, $CH_2=CCH_3COO-CF_2CF(CF_3)_2$, $CH_2=CCH_3COO-nC_5F_{11}$, $CH_2=CCH_3COO-nC_6F_{13}$, $CH_2=CCH_3COO-nC_8F_{17}$, $CH_2=CCH_3COO-CH_2CF_3$, $CH_2=CCH_3COO-CH(CF_3)_2$, $CH_2=CCH_3COO-CH_2CH(CF_3)_2$, $CH_2=CCH_3COO-CH_2(CF_2)_2F$, $CH_2=CCH_3COO-CH_2(CF_2)_3F$, $CH_2=CCH_3COO-CH_2(CF_2)_4F$, $CH_2=CCH_3COO-CH_2(CF_2)_6F$, $CH_2=CCH_3COO-CH_2(CF_2)_8F$, $CH_2=CCH_3COO-CH_2CH_2CF_3$, $CH_2=CCH_3COO-CH_2CH_2(CF_2)_2F$, $CH_2=CCH_3COO-CH_2CH_2(CF_2)_3F$, $CH_2=CCH_3COO-CH_2CH_2(CF_2)_4F$, $CH_2=CCH_3COO-CH_2CH_2(CF_2)_6F$, $CH_2=CCH_3COO-CH_2CH_2(CF_2)_8F$, $CH_2=CCH_3COO-CH_2CH_2CH_2CF_3$, $CH_2=CCH_3COO-CH_2CH_2CH_2(CF_2)_2F$, $CH_2=CCH_3COO-CH_2CH_2CH_2(CF_2)_2H$, $CH_2=CCH_3COO-CH_2(CF_2)_4H$, $CH_2=CCH_3COO-CH_2CH_2(CF_2)_3H$, $CH_2=CCH_3COO-CH_2CH_2CF(CF_3)-[OCF_2CF(CF_3)]_z-OC_3F_7$, $CH_2=CCH_3COO-CH_2CH_2CF_2CF_2-[OCF_2CF(CF_3)]_z-OC_3F_7$ $CH_2=CHCOO-CF_3$, $CH_2=CHCOO-C_2F_5$, $CH_2=CHCOO-nC_3F_7$, $CH_2=CHCOO-CF(CF_3)_2$, $CH_2=CHCOO-nC_4F_9$, $CH_2=CHCOO-CF_2CF(CF_3)_2$, $CH_2=CHCOO-nC_5F_{11}$, $CH_2=CHCOO-nC_6F_{13}$, $CH_2=CHCOO-nC_8F_{17}$, $CH_2=CHCOO-CH_2CF_3$, $CH_2=CHCOO-CH(CF_3)_2$, $CH_2=CHCOO-CH_2CH(CF_3)_2$, $CH_2=CHCOO-CH_2(CF_2)_2F$, $CH_2=CHCOO-CH_2(CF_2)_3F$, $CH_2=CHCOO-CH_2(CF_2)_4F$, $CH_2=CHCOO-CH_2(CF_2)_6F$, $CH_2=CHCOO-CH_2(CF_2)_8F$, $CH_2=CHCOO-CH_2CH_2CF_3$, $CH_2=CHCOO-CH_2CH_2(CF_2)_2F$, $CH_2=CHCOO-CH_2CH_2(CF_2)_3F$, $CH_2=CHCOO-CH_2CH_2(CF_2)_4F$, $CH_2=CHCOO-CH_2CH_2(CF_2)_6F$, $CH_2=CHCOO-CH_2CH_2CH_2CF_3$, $CH_2=CHCOO-CH_2CH_2CH_2(CF_2)_2F$, $CH_2=CHCOO-CH_2CH_2CH_2(CF_2)_2H$, $CH_2=CHCOO-CH_2(CF_2)_4H$, $CH_2=CHCOO-CH_2CH_2(CF_2)_3H$, $CH_2=CHCOO-CH_2CH_2CF(CF_3)-[OCF_2CF(CF_3)]_z-OC_3F_7$, and $CH_2=CHCOO-CH_2CH_2CF_2CF_2-[OCF_2CF(CF_3)]_z-OC_3F_7$. Among these, the vinyl monomers represented by the following formulae are preferred. $CH_2=CHCOO-CH_2CH_2(CF_2)_6F$, $CH_2=CHCOO-CH_2CH_2(CF_2)_8F$, $CH_2=CCH_3COO-CH_2CH_2(CF_2)_6F$, $CH_2=CCH_3COO-CH_2CH_2(CF_2)_8F$, $CH_2=CHCOO-CH_2CF_3$, and $CH_2=CCH_3COO-CH_2CF_3$. The vinyl monomers represented by the following formulae are particularly preferred. $CH_2=CHCOO-CH_2CF_3$, and $CH_2=CCH_3COO-CH_2CF_3$.

The copolymer of the present invention can be synthesized by copolymerizing at least (A) unsaturated monomers having a carbosiloxane dendrimer structure and (B) unsaturated monomers not having long-chain alkyl groups of from 14 to 22 carbon atoms. However, the copolymer of the present invention is preferably polymerized under conditions in which the percentage of unsaturated monomers of component A having a carbosiloxane dendrimer structure is from 45 to 60% by mass out of all of the monomers. When the amount of the component (A) that is used is less than 45% by mass, a copolymer having a carbosiloxane dendrimer structure precipitates in a system containing a large amount of an ultraviolet absorber, which results in poor compounding stability. In addition, with regard to the film properties, even if the glass transition point of the copolymer is adjusted by the component (B) and the film strength is adjusted to yield desired physical properties, the hard texture remains, and when this is applied to the skin or hair as a cosmetic, there is a problem in that there is a strong coating feeling. On the other hand, when the component (A) is greater than 60% by mass, the compounding stability is improved, but the molecular weight of the copolymer may not improve to the target molecular weight due to the steric hindrance of the carbosiloxane dendrimer structure. In this case, it is difficult to synthesize the copolymer, so this is inappropriate for achieving the objective of the present invention.

Further, while using the component (A) within the range described above, it is possible to simultaneously adjust the type and reaction amount of the monomer components of the component (B) and adjust the calculated glass transition point (Tg) of the copolymer so as to adjust the film characteristics of the copolymer of the present invention within a desired range. Specifically, adjusting the type and amount of the component (B) so that the calculated glass transition point (Tg) is from 40 to 90 degrees is preferable in order to demonstrate the target water resistance, sebum resistance, and film durability using the copolymer of the present invention. In particular, it is most preferable for the copolymer to be designed so that at least two types of the component (B) are used and so that the mass ratio of component (A) and component (B) is within the range of (A):(B)=0.45 to 0.55:0.55 to 0.45 and the calculated glass transition point (Tg) is within the range of from 45 to 85 degrees.

A radical polymerization method or an ion polymerization method may be used as the copolymerization method. Among these methods, the radical polymerization method is preferred, and a solution polymerization method is particularly preferably used. The solution polymerization method is carried out by reacting each of the unsaturated monomers in a solvent in the presence of a radical initiator for 3 to 20 hours under temperature conditions ranging from 50 to 150° C. The utilized solvents during such reaction are exemplified by aliphatic hydrocarbons such as hexane, octane, decane, cyclohexane, or the like; aromatic hydrocarbons such as benzene, toluene, xylene, or the like; ethers such as diethyl ether, dibutyl ether, tetrahydrofuran, dioxane, or the like; ketones such as acetone, methyl ethyl ketone, methyl isobutyl ketone, diisobutyl ketone, or the like; esters such as methyl acetate, ethyl acetate, butyl acetate, isobutyl acetate, or the like; alcohols such as methanol, ethanol, isopropyl alcohol, butanol, or the like; and organosiloxane oligomers such as octamethylcyclotetrasiloxane, decamethyl cyclopentasiloxane, hexamethyldisiloxane, octamethyltrisiloxane, or the like. Any conventionally known compound generally used in the radical polymerization method can be employed as the radical initiator. Specific examples of the radical initiator include azobis-based compounds such as 2,2'-azobis(isobutyronitrile), 2,2'-azobis(2-methylbutyronitrile), 2,2'-azobis(2,4-dimethylvaleronitrile), dimethyl-2,2'-azobis (2-methyl propionate), or the like; and organic peroxides such as benzoyl peroxide, lauroyl peroxide, tert-butyl peroxybenzoate, tert-butyl peroxy-2-ethylhexanoate, or the like. The radical initiators may be used alone or in combination of two or more types thereof. The amount of the radical initiator that is used is preferably within the range of from 0.1 to 5 parts by mass with respect to per 100 parts total mass of the components (A) and (B). Moreover, a chain transfer agent can be added during the polymerization. Specific examples of the chain transfer agent include mercapto compounds such as 2-mercaptoethanol, butyl mercaptan, n-dodecyl mercaptan, 3-mercaptopropyltrimethoxysilane, polydimethylsiloxanes having a mercaptopropyl group, or the like; and halogenated compounds such as methylene chloride, chloroform, carbon tetrachloride, butyl bromide, 3-chloropropyltrimethoxysilane, or the like.

After the polymerization, purification may be carried out by means of a method in which the remaining unreacted vinyl-based monomers are removed by heating under reduced pressure or a method in which a deodorant treatment due to a hydrogenation reaction without a solvent or with a solvent is carried out in the presence of a hydrogenation catalyst and light components are removed by distillation by contacting with nitrogen gas under reduced pressure. In particular, in the case of utilization as an external use preparation in which reduction of odors and miscibility with other cosmetic components are needed, the purified product is preferably used. In the hydrogenation reaction and stripping process, solvents, reaction conditions, pressure-reduction conditions, and the like used in the purification of conventional organopolysiloxane copolymers can be used or selected without any restrictions.

In addition, with the objective of further improving the adhesiveness of the vinyl polymer to the skin or hair or imparting moderate washability after use, an amino group may be introduced into the side chain of the vinyl polymer using an amino group-containing vinyl monomer such as dimethylaminoethyl acrylate, dimethylaminoethyl methacrylate, diethylaminoethyl acrylate, or diethylaminoethyl methacrylate as part of the component (B), and this may then be modified with an alkali metal salt, an ammonium salt, an amine salt of a halogenated fatty acid such as a potassium salt of monochloroacetic acid, an ammonium salt of monochloroacetic acid, an aminomethylpropanol salt of monochloroacetic acid, a triethanolamine salt of monobromoacetic acid, or a sodium salt of monochloropropionic acid. Alternatively, a carboxylic acid group may be introduced into the side chain of the vinyl polymer using a carboxylic acid-containing vinyl monomer such as acrylic acid, methacrylic acid, itaconic acid, crotonic acid, fumaric acid, or maleic acid as part of the component (B), and this may then be neutralized with an amine such as triethylamine, diethylamine, or triethanolamine.

The weight average molecular weight of the copolymer of the present invention preferably ranges from 3,000 to 2,000,000, and more preferably ranges from 5,000 to 800,000, from the standpoint of ease of blending in cosmetics. The form of the copolymer is exemplified by liquids, gums, pastes, solids, and powders.

The copolymer of the present invention has film formability and is suitable as a raw material for a cosmetic. Accordingly, the copolymer of the present invention is preferably compounded with a cosmetic.

The compounded amount of the copolymer in the cosmetic of the present invention is not particularly limited, and the cosmetic of the present invention may contain from 0.1 to 90% by mass of the copolymer using the total mass of the cosmetic as a reference. Specifically, the compounded amount of the copolymer can be changed appropriately within the range of from 0.1 to 20% by mass, from 0.5 to 20% by mass, or from 1 to 10% by mass, for example, in accordance with the type of the cosmetic.

<Copolymer Composition>

When compounding the copolymer of the present invention with a cosmetic, the copolymer is preferably in the form of a solution or dispersion in which the copolymer is diluted with a solvent, or a powder. In particular, the copolymer of the present invention is preferably dispersed or diluted with at least one type of oil agent and compounded with the cosmetic in the form of a copolymer composition containing the copolymer described above and at least one type of oil agent. The cosmetic of the present invention may further contain other oil agents.

The copolymer of the present invention has particularly excellent miscibility with various oil agents, and a copolymer composition may be obtained that is uniform over a long time interval. This composition can be compounded with a cosmetic directly and is very useful as a raw material of a cosmetic from the perspective of handling ability and storage stability. More particularly, a copolymer composition formed from 100 parts by mass of the copolymer of the present invention and 5 to 1,000 parts by mass of the oil agent, preferably 50 to 500 parts by mass of the oil agent, and more preferably 100 to 400 parts by mass of the oil agent, may be preferably used. In the case of obtaining the copolymer composition by diluting the copolymer of the present invention with the oil agent, a copolymer in which the solvent and unreacted monomers are removed after the polymerization reaction may be uniformly dispersed in the oil agent by means of mechanical force. Alternatively, the volatile solvent used in the polymerization reaction may be replaced by the oil agent.

<(C) Oil Agent>

Examples of the oil agents include animal oils, plant oils, synthetic oils, or the like that are generally used in cosmetics. As long as the oil agent is hydrophobic, the oil agent may be a solid, semisolid, or liquid, regardless of the source, and may also be non-volatile, semi-volatile, or volatile. The oil agent is used to impart lubricity to the skin or hair, to soften the skin, and to impart a moist feeling. The oil agent may also be used for the purpose of obtaining a copolymer composition by diluting the copolymer of the present invention. In particular, a preferable example is at least one type selected from a silicone oil, a hydrocarbon oil, and a fatty acid ester oil which is a liquid at a temperature of from 5 to 100° C. These oil agents are compounded with the cosmetic of the present invention at the same time as the copolymer composition described above.

Silicone oils are preferred as the oil agent. The silicone oils are hydrophobic as long as they are oil agents, and the molecular structure thereof may be a cyclic, linear, or branched structure. The viscosity of silicone oils at 25° C. is ordinarily within the range of from 0.65 to 100,000 mm$^2$/s and preferably within the range of from 0.65 to 10,000 mm$^2$/s.

Specific examples of the silicone oils include cyclic organopolysiloxanes, linear organopolysiloxanes, and branched organopolysiloxanes. Among these example silicone oils, volatile linear organopolysiloxanes, branched organopolysiloxanes, and cyclic organopolysiloxanes are preferred.

The organopolysiloxanes represented by the following general formulae (3), (4), and (5) can be used as the silicone oils.

[Formula 24]

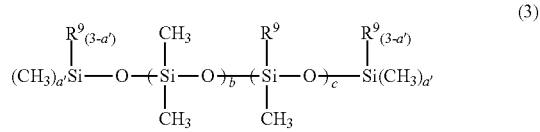

(3)

wherein, $R^9$ is a hydrogen atom, hydroxyl group, or a group selected from monovalent unsubstituted or fluorine- or amino-substituted alkyl groups, aryl groups, or alkoxy groups, having 1 to 30 carbon atoms, and groups represented by $(CH_3)_3SiO[(CH_3)_2SiO]_lSi(CH_3)_2CH_2CH_2$— (where l is an integer ranging from 0 to 1,000);

a' is an integer from 0 to 3;

b is an integer from 0 to 1,000; and c' is an integer from 0 to 1,000, where $1 \le b+c \le 2,000$.

[Formula 25]

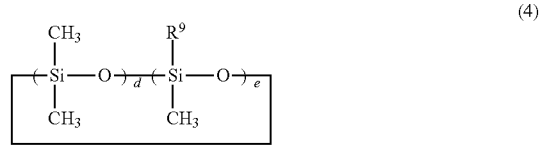

(4)

wherein, $R^9$ is the same as described above;

d is an integer from 0 to 8; and e is an integer from 0 to 8, where $3 \le d+e \le 8$.

[Formula 26]

$R^9_{(4-f)}Si(OSiCH_3)_g$ (5)

wherein,
R⁹ is the same as described above;
f is an integer from 1 to 4; and
g is an integer from 0 to 500.

The monovalent, unsubstituted, or fluorine- or amino-substituted alkyl groups, aryl groups, and alkoxy groups, having 1 to 30 carbon atoms are exemplified by linear or branched alkyl groups having 1 to 30 carbon atoms such as the methyl group, ethyl group, propyl group, butyl group, pentyl group, hexyl group, heptyl group, octyl group, decyl group, dodecyl group, or the like; cycloalkyl groups having 3 to 30 carbon atoms such as the cyclopentyl group, cyclohexyl group, or the like; aryl groups having 6 to 30 carbon atoms such as the phenyl group, tolyl group, xylyl group, naphthyl group, or the like; alkoxy groups having 1 to 30 carbon atoms such as the methoxy group, ethoxy group, propoxy group, or the like; and substituted groups thereof, in which hydrogen atoms bonded to carbon atoms of the aforementioned groups are at least partially substituted by a fluorine atom or amino group. Unsubstituted alkyl groups or aryl groups are preferred, and an unsubstituted alkyl group having 1 to 6 carbon atoms or an aryl group is further preferred. A methyl group, ethyl group, or phenyl group is particularly preferred.

Specifically, examples of silicone oils having the structure described above include cyclic organopolysiloxanes such as hexamethyl cyclotrisiloxane (D3), octamethyl cyclotetrasiloxane (D4), decamethyl cyclopentasiloxane (D5), dodecamethyl-cyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl)trimethylcyclotrisiloxane, 1,3,5,7-tetra(3-methacryloxypropyl)tetramethyl cyclotetrasiloxane, 1,3,5,7-tetra(3-acryloxypropyl)tetramethyl cyclotetrasiloxane, 1,3,5,7-tetra(3-carboxypropyl) tetramethyl cyclotetrasiloxane, 1,3,5,7-tetra(3-vinyloxypropyl)tetramethyl cyclotetrasiloxane, 1,3,5,7-tetra (p-vinylphenyl)tetramethyl cyclotetrasiloxane, 1,3,5,7-tetra [3-(p-vinylphenyl) propyl]tetramethyl cyclotetrasiloxane, 1,3,5,7-tetra(N-acryloyl-N-methyl-3-aminopropyl)tetramethyl cyclotetrasiloxane, 1,3,5,7-tetra(N,N-bis(lauroyl)-3-aminopropyl)tetramethyl cyclotetrasiloxane, and the like.

Examples of straight organopolysiloxanes include a dimethylpolysiloxane in which both molecular terminals are capped with trimethylsiloxy groups (dimethylsilicone with a low viscosity such as 2 mPa·s or 6 mPa·s to dimethylsilicone with a high viscosity such as 1,000,000 mPa·s), organohydrogenpolysiloxane, methylphenylpolysiloxane in which both molecular terminals are capped with trimethylsiloxy groups, a copolymer of methylphenylsiloxane and dimethylsiloxane in which both molecular terminals are capped with trimethylsiloxy groups, diphenylpolysiloxane in which both molecular terminals are capped with trimethylsiloxy groups, a copolymer of diphenylsiloxane and dimethylsiloxane in which both molecular terminals are capped with trimethylsiloxy groups, trimethylpentaphenyltrisiloxane, phenyl(trimethylsiloxy) siloxane, methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl) siloxane and dimethylsiloxane in which both molecular terminals are capped with trimethylsiloxy groups, α,ω-dihydroxypolydimethylsiloxane, α,ω-diethoxypolydimethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, a higher alkoxy-modified silicone, a higher fatty acid-modified silicone, and the like.

Examples of branched organopolysiloxanes include methyltristrimethylsiloxysilane, ethyltristrimethylsiloxysilane, propyltristrimethylsiloxysilane, tetrakistrimethylsiloxysilane, phenyltristrimethylsiloxysilane, or the like.

When at least one type of these silicone oils is included in the cosmetic or the cosmetic raw material of the present invention, the stability over time can be improved, and it is possible to realize the characteristic fresh feel of a silicone oil.

Preferably, oil agents other than silicone oils are liquid at 5 to 100° C. Preferably, oil agents other than silicone oil are hydrocarbon oils and/or fatty ester oils. Such oil agents may be used alone or may be used together with the silicone oil. By using the hydrocarbon oil and/or the fatty acid ester oil in combination with the silicone oil, in addition to the refreshing texture particular to silicone oils, the moisture on the skin is retained, and the cosmetic composition can be imparted with a moisturizing feeling (also called a "refreshing texture") whereby the skin or hair feels moisturized or a smooth texture. In addition, there is the advantage that the stability of the cosmetic over time will not be lost. Furthermore, with a cosmetic composition comprising the hydrocarbon oil and/or fatty acid ester oil and the silicone oil, these moisturizing components can be applied more stably and uniformly on the skin or hair, the moisturizing effects of the moisturizing component on the skin are improved and, compared to a cosmetic composition comprising only the oil agent other than the silicone oil (the hydrocarbon oil and/or fatty ester oil), a smoother, richer feeling to touch is imparted.

Examples of the hydrocarbon oil include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, and the like.

Examples of the fatty acid ester oil include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri-2-ethylhexanoate, trimethylolpropane tri-2-ethylhexanoate, ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl)N-lauroyl-L-glutamate, di(cholesteryl/octyldodecyl)N-lauroyl-L-glutamate, di(phytosteryl/behenyl/octyldodecyl) N-lauroyl-L-glutamate, di(phytosteryl/octyldodecyl)N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, tridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate) (hexyldecanoic acid/sebacic acid)diglyceryl oligoester, glycol distearate (ethylene glycol distearate), diisopropyl dimer dilinoleate, diisostearyl dimer dilinoleate, di(isostearyl/phytosteryl)dimer dilinoleate, (phytosteryl/behenyl)dimer dilinoleate, (phytosteryl/isostearyl/cetyl/stearyl/behenyl)dimer dilinoleate, dimer dilinoleyl dimer dilinoleate, dimer dilinoleyl diisostearate, dimer dilinoleyl hydrogenated rosin condensate, dimer dilinoleic acid hardened castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri (caprylate/ca prate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hardened castor oil, ethyl ester of avocado fatty acid, isopropyl ester of lanolin fatty acid, and the like.

In addition to the above, fats and oils, higher alcohols, higher fatty acids, fluorine-based oils, or the like may be used in combination of two or more types thereof. For example, the oil agents described below may also be used in combination of two or more types. Hereinafter, the oil agents other than silicone oils, hydrocarbon oils, and fatty acid ester oils that can be used in the present invention will be described in detail.

Examples of such fats and oils include natural animal or plant fats and oils and semi-synthetic fats and oils such as avocado oil, linseed oil, almond oil, ibota wax, *perilla* oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, *camellia* oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene".

Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesterol ether, monostearyl glycerol ether (batyl alcohol), monooleyl glycerol ether (selachyl alcohol), and the like.

Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of the fluorine-based oil include perfluoropolyether, perfluorodecalin, perfluorooctane, and the like.

The copolymer of the present invention has excellent film formability, and a treatment powder with an improved feel of use and excellent water resistance, sebum resistance, and the like can be obtained by forming a film on a surface such as a powder in addition to the skin or hair. Accordingly, the copolymer or a copolymer composition of the present invention containing the copolymer is also useful as a surface treatment agent and can not only be used directly as a cosmetic raw material, but can also be suitably used to make a powder water repellent. In addition, a powder composition consisting of a powder or the like treated with the copolymer or copolymer composition of the present invention is also useful as a cosmetic raw material.

<(D) Powder or Coloring Agent>

A cosmetic containing the copolymer or copolymer composition of the present invention may further optionally contain powders or coloring agents, particularly powders (including powders/pigments used as coloring agents) used in cosmetics.

The powder and/or coloring agent can be any powder provided that it is normally used in cosmetic compositions, and is not limited to form (sphere, bar, needle, plate, amorphous, spindle, or the like), particle diameter (aerosol, micro-particle, pigment-grade particle, or the like), or particle structure (porous, nonporous, or the like) thereof. When compounding the powder and/or coloring agent as a pigment, preferably one or two or more selected from an inorganic pigment powder, an organic pigment powder, and a resin powder having an average particle diameter in a range from 1 nm to 20 μm is compounded.

Specific examples of the powders or coloring agents include inorganic powders, organic powders, surfactant metal salt powders (metallic soaps), colored pigments, pearl pigments, metal powder pigments, silicone elastomer powders, or the like. In addition, composite products of these pigments may also be used. Further, this powder or coloring agent includes powders and coloring agents that function as an ultraviolet light blocking component.

Specific examples of inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, dicalcium phosphate, alumina, aluminum hydroxide, boron nitride, and the like. Examples of organic powders include polyamide powder, polyester powder, polyethylene powder, polypropylene powder, polystyrene powder, polyurethane powder, benzoguanamine powder, polymethylbenzoguanamine powder, polytetrafluoroethylene powder, polymethyl methacrylate powder, cellulose, silk powder, nylon powder, nylon 12, nylon 6, silicone powder, silicone rubber powder, silicone elastomer spherical powder surface-coated with polymethylsilsesquioxane, polymethylsilsesquioxane spherical powder, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, macrocrystalline fiber powder, starch powder, lauroyl lysine, and the like. Examples of surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like. Examples of colored pigments include inorganic red pigments such as red iron oxide, iron oxide, iron hydroxide, iron titanate, and the like; inorganic brown pigments such as gamma-iron oxide and the like; inorganic yellow pigments such as yellow iron oxide, ocher, and the like; inorganic black iron pigments such as black iron oxide, carbon black and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, laked pigments of natural pigments such as carminic acid, laccaic acid, carthamin, brazilin, crocin, and the like. Examples of pearl pigments include titanium oxide-coated mica, titanium mica, iron oxide-coated titanium mica, titanium oxide-coated mica, bismuth oxychloride, titanium oxide-coated bismuth oxychloride, titanium oxide-coated talc, fish scale foil, titanium oxide-coated colored mica, and the like. Examples of the metal powder pigment include powders of metals such as aluminum, gold, silver, copper, platinum, stainless steel, and the like.

The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the side chain or the molecular terminal and a diorganopolysiloxane having an unsaturated hydrocarbon group such as an alkenyl group and the like on the side chain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented.

The silicone elastomer powder can be in various forms such as spherical, flat, amorphous, and the like. The silicone elastomer powder may be in the form of an oil dispersion. With the cosmetic composition of the present invention, a silicone elastomer powder having a particle shape, having a primary particle size in a range of 0.1 to 50 μm observed using an electron microscope and/or the average primary particle size in a range of 0.1 to 50 μm measured by laser diffraction/scattering method, and having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

The silicone elastomer powder may optionally be surface treated using silicone resin, silica, or the like. Examples of the surface treatment include those described in Japanese Unexamined Patent Application Publication Nos. H02-243612, H08-12545, H08-12546, H08-12524, H09-241511, H10-36219, H11-193331, and 2000-281523. Note that the crosslinking silicone powder as recited in "Standards of Cosmetic Components by Category" corresponds to the silicone elastomer powder. Commercially available products as the silicone elastomer powder are exemplified by Trefil E-506S, Trefil E-508, 9701 Cosmetic Powder, and 9702 Powder, manufactured by Dow Corning Toray Co., Ltd., or the like.

Furthermore, the powder or coloring agent is preferably partially or entirely subjected to a water-repellent treatment. Additionally, a product can be used in which these powders or coloring agents are compounded together; or subjected to surface treatment using a general oil agent, a silicone oil other than the organopolysiloxane copolymer according to the present invention, a fluorine compound, a surfactant, or the like. One type thereof or two or more types thereof can be used, as necessary. The compounded amount of these powders or coloring agents is preferably within the range of from 0.1 to 99% by mass of the entire cosmetic. In particular, the compounded amount for a powdered solid cosmetic is preferably within the range of from 80 to 99% by mass of the entire cosmetic.

Examples of other water-repellent treatments include various treatments in which the powder or coloring agent is surface treated with a water repellency agent. Specific examples thereof include organosiloxane treatments such as a methylhydrogenpolysiloxane treatment, a silicone resin treatment, a silicone gum treatment, an acryl silicone treatment, a fluorinated silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; and acryl treatments such as an alkyl acrylate treatment and the like. One of the treatments described above can be used or a combination of two or more can be used.

The powders or coloring agents described above are preferably treated using other powder dispersants or surface treatment agents. In particular, the powders or coloring agents may be dispersed or surface-treated by the novel powder treatment agents and treatment methods proposed by the inventors of the invention of the present application in International Patent Publication No. WO2009/022621, Japanese Unexamined Patent Application Publication No. 2011-148784, Japanese Unexamined Patent Application Publication No. 2011-149017, Japanese Unexamined Patent Application Publication No. 2011-246704, Japanese Unexamined Patent Application Publication No. 2011-246705, Japanese Unexamined Patent Application Publication No. 2011-246706, International Patent Publication No. WO2009/022621, International Patent Publication No. WO2011/049246, International Patent Publication No. WO2011/049248, Japanese Patent Application 2011-286973, and the like, or treated to form a slurry using these novel powder treatment agents and the aforementioned oil agents. These novel treatment agents have an excellent improving effect on the unique texture and performance such as dispersion stability, so improving effects on the functionality, texture, storage stability, and the like of the cosmetic can be anticipated when used in combination with the novel cosmetic raw material of the present invention.

<(E) Surfactant>

A cosmetic containing the copolymer or copolymer composition of the present invention may further contain at least one or two or more types of surfactants selected from the group consisting of anionic surfactants, cationic surfactants, nonionic surfactants, and amphoteric surfactants. The compounded amount of the surfactants can be designed appropriately in accordance with the type of the cosmetic or the purpose of the use of the surfactants, but the surfactants can be added within a range of from 0.1 to 90% by mass of the entire cosmetic in order to improve the washing characteristics, and the surfactants are preferably compounded at an amount of at least 25% by mass from the perspective of washability. On the other hand, when compounded for the purpose of emulsifying or dispersing the respective components of the cosmetic such as oil agents and powders, the surfactants can be compounded within the range of from 0.1 to 50 wt. % (mass %), and the range of from 1 to 20% by mass is further preferable.

Specific examples of anionic surfactants include saturated or unsaturated fatty acid salts (for example, sodium laurate, sodium stearate, sodium oleate, sodium linolenate, or the like), alkyl sulfates, alkyl benzene sulfonic acids (for example, hexylbenzene sulfonic acid, toctyl benzene sulfonic acid, dodecyl benzene sulfonic acid, or the like) and salts thereof, polyoxyalkylene alkyl ether sulfates, polyoxyalkylene alkenyl ether sulfates, polyoxyethylene alkyl sulfuric acid ester salts, sulfosuccinic acid alkyl ester salts, polyoxyalkylene sulfosuccinic acid alkyl ester salts, polyoxyalkylene alkyl phenyl ether sulfates, alkane sulfonates, octyl trimethyl ammonium hydroxide, dodecyl trimethyl ammonium hydroxide, alkyl sulfonates, polyoxyethylene alkyl phenyl ether sulfonates, polyoxyalkylene alkyl ether acetates, alkyl phosphates, polyoxyalkylene alkyl ether phosphates, acyl glutamates, α-acyl sulfonates, alkyl sulfonates, alkyl allyl sulfonates, α-olefin sulfonates, alkyl naphthalyne sulfonates, alkane sulfonates, alkyl or alkenyl sulfonates, alkyl amide sulfonates, alkyl or alkenyl phosphates, alkyl amide phosphates, alkyloyl alkyl taurine salts, N-acyl amino acid salts, sulfosuccinates, alkyl ether carboxylates, amide ether carboxylates, α-sulfo fatty acid ester salts, alanine derivatives, glycin derivatives, and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. In particular, a polyoxyalkylene-modified silicone, a polyglyceryl-modified silicone, a glyceryl-modified silicone, or a sugar alcohol-modified silicone may be advantageously subjected to alkyl branching, straight-chain silicone branching, siloxane dendrimer branching, or the like simultaneously with a hydrophilic group as necessary.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specifically, examples include imidazoline-type amphoteric surfactants such as 2-undecyl-N,N,N-(hydroxyethylcarboxymethyl)-2-imidazoline sodium, 2-cocoyl-2-imidazolinium hydroxide-1-carboxyethyloxy disodium salt, and the like; alkylbetaine-type amphoteric surfactants such as lauryl dimethylaminoacetic betaine, myristyl betaine, and the like; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, oleic acid amidopropyl dimethylamino acetic acid betaine, and the like; alkylsulfobetaine-type amphoteric surfactants such as coconut oil fatty acid dimethyl sulfopropyl betaine and the like; alkyl hydroxy sulfobetaine-type amphoteric surfactants such as lauryl dimethylaminohydroxy sulfobetaine and the like; phosphobetaine-type amphoteric surfactants such as laurylhydroxy phosphobetaine and the like; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbon atoms, alkoxyethyl dihydroxyethylamine oxides having from 8 to 18 carbon atoms, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The cosmetic of the present invention may contain various other cosmetic raw materials in addition to the components described above. These raw materials are preferably hydrophobic, having absolutely no solubility in water at room temperature or a solubility of less than 1% by mass per 100 g of water. In addition to the (E) powders or coloring agents described above, examples of such cosmetic raw materials include, (F) an oil-soluble gelling agent, (G) an organically modified clay mineral, (H) a silicone resin, (I) a silicone rubber, (J) a silicone elastomer, (K) an organically modified silicone, and (L) an ultraviolet light blocking component.

<(F) Oil-Soluble Gelling Agent>

Examples of the oil-soluble gelling agent include aluminum stearate, magnesium stearate, zinc myristate, and similar metal soaps; N-lauroyl-L-glutamic acid, α,γ-di-n-butylamine, and similar amino acid derivatives; dextrin palmitate, dextrin stearate, dextrin 2-ethylhexanoate palmitate, and similar dextrin fatty acid esters; sucrose palmitate, sucrose stearate, and similar sucrose fatty acid esters; monobenzylidene sorbitol, dibenzylidene sorbitol, and similar benzylidene derivatives of sorbitol; and the like. One or two or more types of these oil-soluble gelling agent can be used as necessary.

<(G) Organically Modified Clay Mineral>

Examples of the organo-modified clay mineral include dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate, and the like. Examples of commercially available products include Benton 27 (benzyldimethylstearylammonium chloride-treated hectorite, manufactured by Nationalred Co.), Benton 38 (distearyldimethylammonium chloride-treated hectorite, manufactured by Nationalred Co.), and the like.

<(H) Silicone Resin>

The silicone resin is an organopolysiloxane having a highly branched structure, reticular structure, or cage-like structure which is a liquid or a solid at room temperature, and any silicone resin that is ordinarily used in cosmetics may be used as long as the silicone resin does not conflict with the purpose of the present invention. Examples of the solid silicone resin include MQ resins, MDQ resins, MTQ resins, MDTQ resins, TD resins, TQ resins, and TDQ resins formed from arbitrary combinations of triorganosiloxy units (M units) (where the organo groups are only methyl groups, or are methyl groups and vinyl groups or phenyl groups), diorganosiloxy units (D units) (where the organo groups are only methyl groups, or are methyl groups and vinyl groups or phenyl groups), monoorganosiloxy units (T units) (where the organo groups are methyl groups, vinyl groups, or phenyl groups), and siloxy units (Q units). Furthermore, other examples include trimethylsiloxysilicate, polyalkylsiloxysilicate, dimethylsiloxy unit-containing trimethylsiloxysilicate, and alkyl(perfluoroalkyl)siloxysilicate. These silicone resins are oil-soluble and are preferably soluble in D4 or D5.

<(I) Silicone Rubber>

Silicone rubber is a straight-chained diorganopolysiloxane with an ultra-high degree of polymerization and is also called silicone raw rubber or organopolysiloxane rubber. Silicone raw rubber is differentiated from the oily silicones described above because the degree of polymerization of silicone raw rubber is high and, as a result, silicone raw rubber has a degree of plasticity that is measurable. Examples of such a silicone raw rubber include substituted or unsubstituted organopolysiloxanes having dialkylsiloxy units (D units) such as dimethylpolysiloxanes, methylphenylpolysiloxanes, aminopolysiloxanes, and methylfluoroalkylpolysiloxanes or substances having finely crosslinked structures thereof. A representative example is a substance represented by the general formula: $R^{10}(CH_3)_2SiO[CH_3]_2SiO]_2[(CH_3)R^{11}SiO]_tSi(CH_3)_2R^{10}$ (wherein $R^{11}$ is a group selected from a vinyl group, a phenyl group, an alkyl group having from 6 to 20 carbon atoms, an aminoalkyl group having from 3 to 15 carbon atoms, a perfluoroalkyl group having from 3 to 15 carbon atoms, and a quaternary ammonium salt group-containing alkyl group having from 3 to 15 carbon atoms, and the terminal group $R^{10}$ is a group selected from an alkyl group having from 1 to 8 carbon atoms, a phenyl group, a vinyl group, an aminoalkyl group having from 3 to 15 carbon atoms, a hydroxyl group, and an alkoxy group having from 1 to 8 carbon atoms. Additionally, s is from 2,000 to 6,000, t is from 0 to 1,000, and s+t is from 2,000 to 6,000. Of these, a dimethylpolysiloxane raw rubber having a degree of polymerization of 3,000 to 20,000 is preferable.

<(J) Silicone Elastomer>

A silicone elastomer may be compounded with a cosmetic in any form in accordance with the purpose thereof but is particularly preferably compounded as the silicone elastomer powder or crosslinking organopolysiloxane described above. Note that the silicone elastomer powder may be used in the form of an aqueous dispersion liquid in the cosmetic composition of the present invention. Examples of such commercially available aqueous dispersion liquids include BY29-129, and PF-2001 PIF Emulsion manufactured by Dow Corning Toray Co., Ltd. Compounding an aqueous dispersion (suspension) of these silicone elastomer powders is extremely useful in that the feel of use of the cosmetic of the present invention can be further improved.

A preferable crosslinking organopolysiloxane is a non-emulsifying organopolysiloxane having a structure in which the organopolysiloxane chain is three-dimensionally crosslinked by means of a reaction with a crosslinking component or the like and not having a hydrophilic part such as a polyoxyalkylene unit. Any crosslinking organopolysiloxane can be used without limitations to physical modes or preparation methods such as dilution, properties, and the like, provided that it is a crosslinking organopolysiloxane. Particularly preferable examples include α,ω-diene crosslinking silicone elastomers (commercially available products include DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation, in the USA) described in U.S. Pat. No. 5,654,362.

<(K) Organo-Modified Silicone>

An organo-modified silicone is preferably oleophilic. Specific examples include amino-modified silicones, amino polyether-modified silicones, epoxy-modified silicones, carboxyl-modified silicones, amino acid-modified silicones, carbinol-modified silicones, acryl-modified silicones, phenol-modified silicones, amide alkyl-modified silicones, aminoglycol-modified silicones, and alkoxy-modified silicones. In addition to polysiloxane bonds, these organo-modified silicones may have an alkylene chain, an aminoalkylene chain, or a polyether chain to a degree that the compound does not have hydrophilicity as the main chain, and the organo-modified groups may be present on the side chain and/or terminals of the polysiloxane chain. When the cosmetic of the present invention is used as a hair cosmetic, an amino-modified silicone, a carbinol-modified silicone, an amino polyether-modified silicone, or an aminoglycol-modified silicone may be preferably used, and typical examples are amino-modified silicones having 3-aminopropyl groups, N-(2-aminoethyl)-3-aminopropyl groups, or the like.

<(L) Ultraviolet Light Blocking Component>

The ultraviolet light blocking component can be an inorganic ultraviolet light blocking component or an organic ultraviolet light blocking component. In cases where the cosmetic composition of the present invention needs to have sunblocking effects, preferably at least one type of inorganic or organic, and particularly preferably an organic ultraviolet light blocking component is compounded. The copolymer of the invention of the present application typically has excellent compatibility with hardly soluble organic ultraviolet light blocking components such as diethylamino hydroxybenzoyl hexyl benzoate known as "Uvinul A", bis-ethylhexyloxyphenol methoxyphenyl triazine known as "Tinosorb S", 2-cyano-3,3-diphenylpropa-2-enoic acid 2-ethylhexyl ester known as "Octocrilene", and other cinnamic acid-based ultraviolet absorbers, for example, and can improve the compounding stability with the copolymer of the invention of the present application.

The inorganic ultraviolet light blocking component may be compounded as an ultraviolet light scattering agent such as the inorganic pigment powders and metal powder pigments mentioned above. Examples thereof include metal oxides such as titanium oxide, zinc oxide, cerium oxide, titanium suboxide, iron-doped titanium oxides, and the like; metal hydroxides such as iron hydroxides and the like; metal flakes such as platy iron oxide, aluminum flake, and the like; and ceramics such as silicon carbide, and the like. Of these, at least one type of a material selected from fine particulate metal oxides and fine particulate metal hydroxides with an average particle diameter in a range from 1 to 100 nm and a particulate, plate-like, needle-like, or fiber form is preferable. These powders are preferably subjected to conventionally known surface treatment such as, for example, fluorine compound treatment (of which perfluoroalkyl phosphate treatment, perfluoroalkylsilane treatment, perfluoropolyether treatment, fluorosilicone treatment, and fluorinated silicone resin treatment are preferable), silicone treatment (of which methylhydrogen polysiloxane treatment, dimethylpolysiloxane treatment, and vapor-phase tetramethyltetrahydrogen cyclotetrasiloxane treatment are preferable), silicone resin treatment (of which trimethylsiloxysilicic acid treatment is preferable), pendant treatment (which is a method of adding alkyl chains after vapor-phase silicone treatment), silane coupling agent treatment, titanium coupling agent treatment, silane treatment (of which alkylsilane or alkylsilazane treatment is preferable), oil agent treatment, N-acylated lysine treatment, polyacrylic acid treatment, metal soap treatment (of which a stearic acid or myristic acid salt is preferable), acrylic resin treatment, metal oxide treatment, or the like, and the powders are preferably treated with a plurality of these treatments. For example, the surface of the fine particulate titanium oxide can be coated with a metal oxide such as silicon oxide and alumina, and, thereafter, surface treating using an alkylsilane can be carried out. A total amount of the surface treatment agent is preferably in a range from 0.1 to 50% by mass of the powder.

The organic ultraviolet light blocking component is an oleophilic ultraviolet light blocking component, examples of which include benzoic acid-based ultraviolet absorbers such as para amino benzoic acid (hereafter abbreviated as PABA), PABA monoglycerin esters, N,N-dipropoxy PABA ethyl esters, N,N-diethoxy PABA ethyl esters, N,N-dimethyl PABA ethyl esters, N,N-dimethl PABA butyl esters, and diethylamino hydroxybenzoyl hexyl benzoate; anthranilic acid-based ultraviolet absorbers such as homomenthyl-N-acetyl anthranilate; salicylic acid-based ultraviolet absorbers such as amyl salicylate, menthyl salicylate, homomenthyl salicylate, octyl salicylate, phenyl salicylate, benzyl salicylate, and p-isopropanol phenyl salicylate; cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate, glyceryl mono-2-ethylhexanoyl-diparamethoxycinnamate, and 3,4,5-trimethoxycinnamic acid 3-methyl-4-[methyl-bis(trimethylsiloxy)silyl]butyl; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophone, 2-hydroxy-4-methoxy-4'-methylbenzophone, 2-hydroxy-4-methoxybenzophone-5-sulfonate, 4-phenylbenzophone, 2-ethylhexyl-4'-phenylbenzophone-2-carboxylate, hydroxy-4-n-octylbenzophone, and 4-hydroxy-3-carboxybenzophenone; 3-(4'-methylbenzylidene)-d,l-camphor, 3-benzylidene-d,l-camphor, urocanic acid, ethyl urocanate ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dianisoylmethane, 4-methoxy-4'-t-butyldibenzoyl methane, and 5-(3,3-dimethyl-2-norbornylidene)-3-pentane-2-on.

Additionally, it is possible to use a product in which the organo-ultraviolet light blocking component is comprised in a hydrophobic polymer powder. The polymer powder may be hollow, and preferably has an average primary particle size in a range from 0.1 to 50 μm. Particle size distribution may be broad or sharp. Types of polymer include acrylic resins, methacrylic resins, styrene resins, polyurethane resins, polyethylene, polypropylene, polyethylene terephthalate, silicone resins, nylons, acrylamide resins, and silylated polypeptide resins. A polymer powder comprising from 0.1 to 30% by mass of an organic ultraviolet light blocking component is preferable, and a polymer powder comprising 4-tert-butyl-4'-methoxydibenzoylmethane, which is a UV-A absorber, is particularly preferable.

The ultraviolet light blocking component that can be preferably used in the cosmetic of the present invention is at least one type selected from the group consisting of fine particulate titanium oxide, fine particulate zinc oxide, 2-ethylhexyl paramethoxycinnamate, 4-tert-butyl-4'-methoxydibenzoylmethane, diethylamino hydroxybenzoyl hexyl benzoate, bis-ethylhexyloxyphenol methoxyphenyl triazine, 2-cyano-3,3-diphenylpropa-2-enoic acid 2-ethylhexyl ester, and other benzophenone-based ultraviolet absorbers. These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

<(M) Water-Soluble Polymer>

On the other hand, the cosmetic of the present invention may be a water-soluble aqueous or emulsion-type cosmetic having a high water-soluble content, and it is possible and preferable to compound (M) a water-soluble polymer in accordance with the dosage form. One type or two or more types of water-soluble polymers may be used as water-soluble polymers. Examples of natural water-soluble polymers include vegetable-based polymers such as gum Arabic, tragacanth gum, galactan, guar gum, carob gum, karaya gum, carrageenan, pectin, agar, quince seed (*Cydonia oblonga*), algal colloid (seaweed extract), starch (rice, corn, potato, or wheat), glycyrrhizinic acid, and the like; microorganism-based polymers such as xanthan gum, dextran, succinoglucan, pullulan, and the like; and animal-based polymers such as collagen, casein, albumin, gelatin, and the like. Additionally, examples of semisynthetic water-soluble polymers include starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate, and the like. Examples of synthetic water-soluble polymers include vinyl-based polymers such as polyvinylalcohol, polyvinyl methyl ether-based polymers, polyvinylpyrrolidone, carboxyvinyl polymers (CARBOPOL 940, CARBOPOL 941; manufactured by B.F. Goodrich Corporation); polyoxyethylene-based polymers such as polyethyleneglycol 20,000, polyethyleneglycol 6,000 and polyethyleneglycol 4,000; copolymer-based polymers such as polyoxyethylene-polyoxypropylene copolymers and PEG/PPG methyl ethers; acryl-based polymers such as polysodium acrylate, polyethyl acrylate, and polyacrylamide; polyethylene imines; and cationic polymers. Examples of other cationic water-soluble polymers, in particular, as components which are preferably compounded in hair cosmetic compositions, include quaternary nitrogen-modified polysaccharides (e.g. cation-modified cellulose, cation-modified hydroxyethylcellulose, cation-modified guar gum, cation-modified locust bean gum, cation-modified starch, and the like); dimethyldiallylammonium chloride derivatives (e.g. a copolymer of dimethyldiallylammonium chloride and acrylamide, poly(dimethylmethylene piperidinium chloride), and the like); and vinylpyrrolidone derivatives (e.g. a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride, and the like).

The following other components generally used in cosmetic compositions may be added to the cosmetic composition of the present invention, provided that such components do not inhibit the effectiveness of the present invention: alcohols, organic resins, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like. Specific examples of these include, but are not limited to, substances common to those specifically disclosed in paragraphs 0099 to 0113 of Japanese Unexamined Patent Application Publication No. 2011-149017.

The cosmetic of the present invention may also contain natural plant extract components, seaweed extract components, and herbal medicine components in accordance with the purpose thereof. Two or more types of these components may be compounded. Specific examples of these include but are not limited to substances common to those specifically disclosed in paragraph 0115 and the like of Japanese Unexamined Patent Application Publication No. 2011-149017.

In addition to water such as purified water or mineral water, the cosmetic of the present invention may also contain light isoparaffin, ethers, LPG, N-methylpyrrolidone, and next-generation chlorofluorocarbons in accordance with the purpose thereof.

In addition to the copolymer of the present invention, at least one type selected from the group consisting of an acryl silicone dendrimer copolymer, a polyamide-modified silicone, an alkyl-modified silicone wax, and an alkyl-modified silicone resin wax may be used in the cosmetic of the present invention.

Particularly preferable examples of acryl silicone dendrimer copolymers include a vinyl-based polymer having a carbosiloxane dendrimer structure at the side chain such as that described in Japanese Patent No. 4009382 (Japanese Unexamined Patent Application Publication No. 2000-063225). Commercially available products include FA 4001 CM Silicone Acrylate and FA 4002 ID Silicone Acrylate manufactured by Dow Corning Toray Co., Ltd.

An example of a polyamide-modified silicones is the siloxane-based polyamide described in U.S. Pat. No. 5,981,680, and specific examples of commercially available products include 2-8178 Gellant, and 2-8179 Gellant (manufactured by Dow Corning Corporation, in the USA).

The alkyl-modified silicone wax need only be an alkyl-modified silicone wax in wax form at room temperature, and examples thereof include methyl (long chain alkyl) polysiloxanes having both molecular terminals capped with trimethylsiloxy groups, copolymers of a dimethylpolysiloxane having both molecular terminals capped with trimethylsiloxy groups and a methyl (long chain alkyl) siloxane, dimethylpolysiloxane modified with long chain alkyls at both molecular terminals, and the like. Examples of commercially available products include AMS-C30 Cosmetic Wax, 2503 Cosmetic Wax, and the like (manufactured by Dow Corning Corporation, in the USA).

Examples of alkyl-modified silicone resin waxes include the silsesquioxane resin wax described in Japanese Patent Application (Translation of PCT Application) No. 2007-532754.

The cosmetic of the present invention may be in the form of a liquid, an emulsion, a cream, a solid, a paste, a gel, a powder, a multi-layer substance, a mousse, or a spray.

Specific examples of cosmetic products of the present invention include, but are not limited to, skin care products such as skin cleaning agent products, skin care products, makeup products, anti-perspirant products, ultraviolet light blocking products, or the like; hair cosmetics such as hair washing products, hair styling products, hair dye products, baldness remedy products, hair rinse products, hair conditioning products, hair treatment products, or the like; bathing cosmetic products; hair regrowth agents, hair growth promoters, analgesics, germicides, anti-inflammatory agents, refreshing agents, and skin aging prevention agents.

The skin use cosmetic products can be used on any site of the entire body including the scalp, face (including lips, eyebrows, and cheeks), fingers, and fingernails. Specific examples thereof include cleansing gels, cleansing creams, cleansing foams, face washing creams, eye makeup removers, face washing foams, liquid soaps (body soaps), hand soaps, gel-like soaps, shaving creams, nail polish removers, acne treatment cosmetic compositions, and similar skin cleansing agent products; skin creams, scalp treatments, skin milks, milk lotions, emulsions, facial packs, body powders, essences, shaving lotions, massage lotions, and similar skin care products; foundations, liquid foundations, oil-based foundations, makeup bases, powders, face powders, cheek coloring, lip creams, lipsticks, lip glosses, eye creams, mascaras, eyebrow pencils, eyelash cosmetic products, and similar makeup products; deodorants and similar anti-perspirants; and sunscreen agents, tanning use medicaments (sun tanning agent), and similar ultraviolet light blocking products.

Examples of scalp use cosmetic products include shampoos, rinse-in shampoos, and similar hair use cleansing agents; hair waxes, hair use curl holding agents, setting agents, hair creams, hairsprays, hair liquids, and similar hair dressing products; hair coloring substances, hair color sprays, hair color rinses, hair color sticks, and similar hair use coloration products; hair tonics, hair treatment essences, hair packs, and similar hair growing products; and oil rinses, cream rinses, treatment rinses, hair conditioners, hair treatments, and similar hair rinse or hair conditioning products. In addition, examples of bath use cosmetic products include bath foams.

The copolymer of the present invention may be blended in non-cosmetic products for other applications such as various types of external use preparations, paints, coating agents, anti-foaming agents, deodorizing agents, or the like.

EXAMPLES

Hereinafter, the present invention will be described in detail based on Practical Examples and Comparative Examples. However, the present invention is not limited to these Practical Examples. The abbreviations "%" and "parts" respectively refer to "% by mass" and "parts by mass" hereinafter.

Practical Example 1

100 g of isopropyl alcohol (IPA) was placed in a 500 mL four-neck flask equipped with a stirrer, thermometer, and reflux condenser. Nitrogen gas was used for bubbling and performing sufficient degasification, and then the flask was heated to 80° C. Next, 45 g of methyl methacrylate, 10 g of n-butyl acrylate, 45 g of a carbosiloxane dendrimer monomer represented by the following formula (A-1):

[Formula 27]

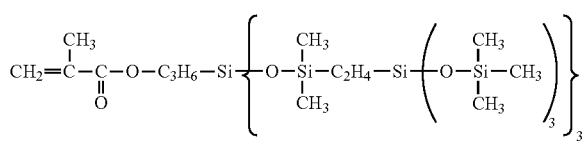

and 1.0 g of 2,2'-azobis-2-methylbutyronitrile (manufactured by Otsuka Chemical Co., Ltd.) were added to a dripping funnel, and the mixture was dissolved. While the monomer mixture was maintained at 80° C. under a nitrogen atmosphere, the dripping funnel was used for drop-wise addition over 2 hours. After completion of drop-wise addition, the mixture was stirred and heated for 6 hours under nitrogen atmosphere. After completion of stirring, the polymerization addition rate of the reaction products was analyzed by gas chromatography. As a result, the addition rate of polymerization was found to be 97%, and it was determined that a vinyl-based polymer was obtained. 250 g of decamethylpentacyclosiloxane was added to the isopropyl alcohol solution of the vinyl-based polymer. Then the IPA was removed by distillation at 120° C. The excess decamethylpentacyclosiloxane and unreacted monomers were distilled out under reduced pressure, and the solid content concentration was adjusted to 30% by mass.

Practical Example 2

100 g of isopropyl alcohol (IPA) was placed in a 500 mL four-neck flask equipped with a stirrer, thermometer, and reflux condenser. Nitrogen gas was used for bubbling and performing sufficient degasification, and then the flask was heated to 80° C. Next, 41 g of methyl methacrylate, 9 g of n-butyl acrylate, 50 g of a carbosiloxane dendrimer monomer represented by the above formula (A-1), and 1.0 g of dimethyl-2,2'-azobis(2-methyl propionate) (manufactured by Wako Pure Chemical Industries, Ltd.) were added to a dripping funnel, and the mixture was dissolved. While the monomer mixture was maintained at 80° C. under a nitrogen atmosphere, the dripping funnel was used for drop-wise addition over 2 hours. After completion of drop-wise addition, the mixture was stirred and heated for 6 hours under nitrogen atmosphere. After completion of stirring, the polymerization addition rate of the reaction products was analyzed by gas chromatography. As a result, the addition rate of polymerization was found to be 98%, and it was determined that a vinyl-based polymer was obtained. Next, 250 g of decamethylpentacyclosiloxane was added to an isopropyl alcohol solution of this vinyl-based polymer. The reaction mixture was transferred to a 1 L autoclave, and 1 g of a sponge nickel catalyst was added to perform hydrogen exchange. After the reaction mixture was heated to 100° C. and oxygen was fed up to 0.8 Mpa, the product was aged while heating for 6 hours. After the catalyst was filtered, the isopropyl alcohol was distilled out under reduced pressure while heating at 120° C., and the decamethylpentacyclosiloxane solvent was exchanged. The hydrogenated unreacted monomers were removed, and the solid content concentration was adjusted to 30% by mass.

Practical Example 3

100 g of isopropyl alcohol (IPA) was placed in a 500 mL four-neck flask equipped with a stirrer, thermometer, and reflux condenser. Nitrogen gas was used for bubbling and performing sufficient degasification, and then the flask was heated to 80° C. Next, 38 g of methyl methacrylate, 12 g of n-butyl acrylate, 50 g of a carbosiloxane dendrimer monomer represented by the above formula (A-1), and 1.0 g of 2,2'-azobis-2-methylbutyronitrile (manufactured by Otsuka Chemical Co., Ltd.) were added to a dripping funnel, and the mixture was dissolved. While the monomer mixture was maintained at 80° C. under a nitrogen atmosphere, the dripping funnel was used for drop-wise addition over 2 hours. After completion of drop-wise addition, the mixture was stirred and heated for 6 hours under nitrogen atmosphere. After completion of stirring, the polymerization addition rate of the reaction products was analyzed by gas chromatography. As a result, the addition rate of polymerization was found to be 97%, and it was determined that a vinyl-based polymer was obtained. After 175 g of decamethylpentasiloxane was added to an isopropyl alcohol solution of this vinyl-based polymer, the IPA was distilled out at 120° C. The excess decamethylpentasiloxane and unreacted monomers were distilled out under reduced pressure, and the solid content concentration was adjusted to 30% by mass.

Practical Example 4

100 g of isopropyl alcohol (IPA) was placed in a 500 mL four-neck flask equipped with a stirrer, thermometer, and reflux condenser. Nitrogen gas was used for bubbling and performing sufficient degasification, and then the flask was heated to 80° C. Next, 38 g of methyl methacrylate, 12 g of 2-ethylhexyl acrylate, 50 g of a carbosiloxane dendrimer monomer represented by the above formula (A-1), and 1.0 g of 2,2'-azobis-2-methylbutyronitrile (manufactured by Otsuka Chemical Co., Ltd.) were added to a dripping funnel, and the mixture was dissolved. While the monomer mixture was maintained at 80° C. under a nitrogen atmosphere, the dripping funnel was used for drop-wise addition over 2 hours. After completion of drop-wise addition, the mixture was stirred and heated for 6 hours under nitrogen atmosphere. After completion of stirring, the polymerization addition rate of the reaction products was analyzed by gas chromatography. As a result, the addition rate of polymerization was found to be 97%, and it was determined that a vinyl-based polymer was obtained. After 250 g of decamethylpentasiloxane was added to an isopropyl alcohol solution of this vinyl-based polymer, the IPA was distilled out at 120° C. The excess decamethylpentasiloxane and unreacted monomers were distilled out under reduced pressure, and the solid content concentration was adjusted to 30% by mass.

Practical Example 5

A copolymer composition with a solid content concentration of 30% by mass was prepared using the same method as in Practical Example 1 with the exception of using dimethylpolysiloxane (viscosity: 2 mPa·s) instead of decamethylpentasiloxane as the dilution solvent in Practical Example 1.

Practical Example 6

A copolymer composition with a solid content concentration of 30% by mass was prepared using the same method as in Practical Example 2 with the exception of using dimethylpolysiloxane (viscosity: 2 mPa·s) instead of decamethylpentasiloxane as the dilution solvent in Practical Example 2.

Practical Example 7

A copolymer composition with a solid content concentration of 30% by mass was prepared using the same method as in Practical Example 3 with the exception of using dimethylpolysiloxane (viscosity: 2 mPa·s) instead of decamethylpentasiloxane as the dilution solvent in Practical Example 3.

Practical Example 8

A copolymer composition with a solid content concentration of 30% by mass was prepared using the same method as in Practical Example 4 with the exception of using dimethylpolysiloxane (viscosity: 2 mPa·s) instead of decamethylpentasiloxane as the dilution solvent in Practical Example 4.

Practical Example 9

A copolymer composition was prepared using the same method as in Practical Example 3 with the exception of using isododecane instead of decamethylpentasiloxane as the dilution solvent in Practical Example 3 and adjusting the solid content concentration of the copolymer to 40% by mass.

Comparative Example 1

A copolymer was synthesized in accordance with the monomer composition described in Practical Example 2 of Japanese Unexamined Patent Application Publication No. 2000-63225, and a copolymer composition formed by diluting the copolymer with decamethylpentasiloxane so that the solid content concentration was 30% by mass was used as a comparative example.

Comparative Example 2

100 g of isopropyl alcohol (IPA) was placed in a 500 mL four-neck flask equipped with a stirrer, thermometer, and reflux condenser. Nitrogen gas was used for bubbling and performing sufficient degasification, and then the flask was heated to 80° C. Next, 55 g of methyl methacrylate, 5 g of 2-ethylhexyl acrylate, 40 g of a carbosiloxane dendrimer monomer represented by the above formula (A-1), and 1.0 g of 2,2'-azobis-2-methylbutyronitrile (manufactured by Otsuka Chemical Co., Ltd.) were added to a dripping funnel, and the mixture was dissolved. While the monomer mixture was maintained at 80° C. under a nitrogen atmosphere, the dripping funnel was used for drop-wise addition over 2 hours. After completion of drop-wise addition, the mixture was stirred and heated for 6 hours under nitrogen atmosphere. After completion of stirring, the polymerization addition rate of the reaction products was analyzed by gas chromatography. As a result, the addition rate of polymerization was found to be 97%, and it was determined that a vinyl-based polymer was obtained. After 250 g of decamethylpentasiloxane was added to an isopropyl alcohol solution of this vinyl-based polymer, the IPA was distilled out at 120° C. The excess decamethylpentasiloxane and unreacted monomers were distilled out under reduced pressure, and the solid content concentration was adjusted to 30% by mass.

[Evaluation 1] The vinyl-based copolymer compositions of Practical Examples 1 to 9 and Comparative Examples 1 and 2 were evaluated as follows with regard to each of the characteristics of water resistance (water repellency), sebum resistance, glass transition point, and tactile sensation. The results are shown in Table 1. In the table, "Compound 1" is a carbosiloxane dendrimer monomer represented by the above formula (A-1).

[Water Resistance (Water Repellency)] After the vinyl-based copolymer was applied to a glass plate, the solvent was removed by drying at room temperature to obtain a vinyl-based polymer coating film. Water droplets were placed on the surface of this coating film, and the contact angle with respect to the water was measured. An automatic contact angle meter (manufactured by Kyowa Interface Chemical Co., Ltd.) was used as a measurement device. An angle of 100 degrees or greater was evaluated as ●, an angle of not less than 90 degrees and less than 100 degrees was evaluated as ○, and an angle of less than 90 degrees was evaluated as Δ.

[Sebum Resistance] After the vinyl-based copolymer was applied to a glass plate, the solvent was removed by drying at room temperature to obtain a vinyl-based polymer coating film. Squalane droplets were placed on the surface of this coating film, and the contact angle with respect to the squalane was measured. An automatic contact angle meter (manufactured by Kyowa Interface Chemical Co., Ltd.) was used as a measurement device. An angle of 50 degrees or greater was evaluated as ●, an angle of not less than 40 degrees and less than 50 degrees was evaluated as ○, and an angle of less than 40 degrees was evaluated as Δ.

[Calculated Glass Transition Point] The glass transition point of the vinyl-based copolymer was calculated from a FOX equation.
The FOX equation of the glass transition point (Tg) is as follows.
Tg is determined by a Fox formula (source: Radical Polymerization Handbook, P 566 (1999))

$$Tg=(\Sigma Wn)/(\Sigma Wn/Tgn),$$

(Wn: monomer weight, Tgn: Tg of a homopolymer of a monomer n, units: K)

[Tactile Sensation] After the vinyl-based copolymer was applied to a glass plate, the solvent was removed by drying at room temperature to obtain a vinyl-based polymer coating film. The tactile sensation of the surface of this coating film was measured by touching the surface with the fingers.

TABLE 1

| Composition (parts by mass) | Practical Examples | | | | | | | | | Comparative Examples | |
|---|---|---|---|---|---|---|---|---|---|---|---|
| | 1 | 2 | 3 | 4 | 5 | 6 | 7 | 8 | 9 | 1 | 2 |
| Methyl methacrylate | 45 | 41 | 38 | 38 | 45 | 41 | 38 | 38 | 38 | 45 | 55 |
| n-Butyl acrylate | 10 | 9 | 12 | 0 | 10 | 9 | 12 | 0 | 12 | 25 | 5 |
| 2-Ethylhexyl acrylate | 0 | 0 | 0 | 12 | 0 | 0 | 0 | 12 | 0 | 0 | 0 |
| Compound 1 (*) | 45 | 50 | 50 | 50 | 45 | 50 | 50 | 50 | 50 | 30 | 40 |
| Dimethyl-2,2'-azobis-(2-methylpropionate) | 1 | 1 | 1 | 1 | 1 | 1 | 1 | 1 | 1 | 1 | 1 |
| Decamethylpentasiloxane | 233 | 233 | 233 | 233 | 0 | 0 | 0 | 0 | 0 | 233 | 233 |
| Dimethylpolysiloxane (Viscosity: 2 mPa · s) | 0 | 0 | 0 | 0 | 233 | 233 | 233 | 233 | 0 | 0 | 0 |
| Isododecane | 0 | 0 | 0 | 0 | 0 | 0 | 0 | 0 | 150 | 0 | 0 |
| Characteristic evaluation results | | | | | | | | | | | |
| Tg (calculated value) | 61 | 61 | 49 | 49 | 61 | 61 | 49 | 49 | 49 | 27 | 83 |
| Water resistance | ● | ● | ● | ● | ● | ● | ● | ● | ● | ● | ● |

TABLE 1-continued

|  | Practical Examples | | | | | | | | | Comparative Examples | |
|---|---|---|---|---|---|---|---|---|---|---|---|
| Composition (parts by mass) | 1 | 2 | 3 | 4 | 5 | 6 | 7 | 8 | 9 | 1 | 2 |
| Sebum resistance | ● | ● | ● | ● | ● | ● | ● | ● | ● | ○ | ○ |
| Tactile sensation | Good | Good | Good | Good | Good | Good | Good | Good | Good | Stickiness | Cracking |

(*) Carbosiloxane dendrimer monomer represented by the above formula (A-1)

[Evaluation 2] The copolymer compositions of Practical Examples 1 to 9 and Comparative Example 1 and 2 were compounded with the following test compositions, and the compounding stability at room temperature and at zero degrees was evaluated. In the evaluation of compounding stability, the test composition was left to stand for one week at room temperature and at zero degrees, respectively, and an evaluation of "dissolution" was made in the event of the uniform dissolution of each component, and an evaluation of "separated" was made in the event of the precipitation/separation of any of the cosmetic raw materials. The evaluation results using the copolymer compositions of Practical Examples 1 to 9 are shown in "Table 2", and the evaluation results using the copolymer compositions of Comparative Examples 1 and 2 are shown in "Table 3".

Specific formulation examples and production examples of the cosmetic of the present invention will be described hereinafter, but it goes without saying that the copolymer of the present invention can also be compounded with other formulas.

In preparation of the formulation examples, the present applicants used the following glycerin-modified organopolysiloxanes A, B, and C having a siloxane dendron structure and diglycerine hydrophilic groups in the molecules as proposed in Japanese Patent Application No. 2011-286973. These are identical to the co-modified organopolisiloxanes P6, P7, and P3 of Practical Examples 6, 7, and 3 in Japanese Patent Application No. 2011-286973 and are produced as follows. In the following compositional formulas, $Me_3SiO$ groups (or $Me_3Si$ group) are notated as "M", $Me_2SiO$ groups

TABLE 2

| | Test composition No. (parts by mass) | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| | Practical Example 1 | | Practical Example 2 | | Practical Example 3 | | Practical Example 4 | | Practical Example 5 | | Practical Example 6 | | Practical Example 7 | | Practical Example 8 | |
| Copolymer | | | | | | | | | | | | | | | | |
| Uvinul A | 2 | | 2 | | 2 | | 2 | | 2 | | 2 | | 2 | | 2 | |
| Octyl methoxycinnamate | 5 | | 5 | | 5 | | 5 | | 5 | | 5 | | 5 | | 5 | |
| Octocrylene | 4 | | 4 | | 4 | | 4 | | 4 | | 4 | | 4 | | 4 | |
| Tinosorb S | 2 | | 2 | | 2 | | 2 | | 2 | | 2 | | 2 | | 2 | |
| Isotridecyl isononanoate | 6 | 0 | 6 | 0 | 6 | 0 | 6 | 0 | 9 | 0 | 9 | 0 | 9 | 0 | 9 | 0 |
| Octyl palmitate | 0 | 6 | 0 | 6 | 0 | 6 | 0 | 6 | 0 | 9 | 0 | 9 | 0 | 9 | 0 | 9 |
| Decamethylpentasiloxane | 11 | | 11 | | 11 | | 11 | | 0 | | 0 | | 0 | | 0 | |
| Dimethylpolysiloxane (Viscosity: 2 mPa · s) | 0 | | 0 | | 0 | | 0 | | 8 | | 8 | | 8 | | 8 | |
| Copolymer | 10 | | 10 | | 10 | | 10 | | 10 | | 10 | | 10 | | 10 | |
| Total | 40 | | 40 | | 40 | | 40 | | 40 | | 40 | | 40 | | 40 | |
| Solubility Room temperature | | | | | | | | | Dissolution | | | | | | | |
| 0 degrees | | | | | | | | | Dissolution | | | | | | | |

TABLE 3

| | Test composition No. (parts by mass) | | | | | |
|---|---|---|---|---|---|---|
| | 17 | 18 | 19 | 20 | 21 | 22 |
| | Comparative Example 1 | | | Comparative Example 2 | | |
| Copolymer | | | | | | |
| Uvinul A | 2 | | | 2 | | |
| Octyl methoxycinnamate | 5 | | | 5 | | |
| Octocrylene | 4 | | | 4 | | |
| Tinosorb S | 2 | | | 2 | | |
| Isotridecyl isononanoate | 6 | 0 | | 6 | 0 | 7 | 8
| Octyl palmitate | 0 | 6 | | 0 | 6 | 0 | 0
| Decamethylpentasiloxane | 11 | | | 11 | | 10 | 9
| Dimethylpolysiloxane (Viscosity: 2 mPa · s) | 0 | | | 0 | | | |
| Copolymer | 10 | | | 10 | | | |
| Total | 40 | | | 40 | | | |
| Solubility Room temperature | | | | Separated | | | |
| 0 degrees | | | | Separated | | | | are notated as "D", and MeHSiO groups are notated as "$D^H$". Units in which a methyl group in D is modified by any substituent is notated as $D^R$.

<Synthesis of Glycerin Co-Modified Organopolysiloxane A>

First, 67.91 g of methylhydrogen polysiloxane represented by the average composition formula $MD_{30}D^H_6M$, 16.03 g of tris-trimethylsiloxy vinyl silane, 7.7 g of diglycerine monoallyl ether, 8.36 g of 1-octene, and 20 g of toluene were added into a reaction vessel and heated to 70° C. while stirring under a stream of nitrogen. Next, 0.100 g of a platinum catalyst was added, and the mixture was reacted for 16 hours. The completion of the reaction was confirmed by an alkali decomposition gas generation method. After the reaction solution was heated at 120° C. under reduced pressure to distill out the low-boiling components, the product was subjected to filtration to obtain a glycerin co-modified organopolysiloxane A having a siloxane dendron structure represented by the average composition formula $MD_{30}D^{R1}_2D^{R4}_1D^{R6}_3M$.

In the formula, $R^1 =\!\!-\!\!C_2H_4Si(OSiMe_3)_3$ $R^4$=hydrophilic group represented by $-\!C_3H_6O-\!X$, wherein X is a diglycerin portion.

$R^6 =\!\!-\!\!C_8H_{17}$

This product was a light yellow transparent liquid.

<Synthesis of Glycerin Co-Modified Organopolysiloxane B>

First, 56.59 g of methylhydrogen polysiloxane represented by the average composition formula $MD_{30}D^H{}_6M$, 13.73 g of tris-trimethylsiloxy vinyl silane, 4.61 g of diglycerine monoallyl ether, 25.07 g of 1-dodecene, and 20 g of toluene were added into a reaction vessel and heated to 70° C. while stirring under a stream of nitrogen. Next, 0.50 g of a platinum catalyst was added, and the mixture was reacted for 20 hours. The completion of the reaction was confirmed by an alkali decomposition gas generation method. After the reaction solution was heated at 120° C. under reduced pressure to distill out the low-boiling components, the product was subjected to filtration to obtain a glycerin co-modified organopolysiloxane B having a siloxane dendron structure represented by the average composition formula $MD_{30}D^{R1}{}_2D^{R4}{}_1D^{R7}{}_3M$.

In this formula, $R^1$ and $R^4$ are synonymous with those described above and $R^7$ has the structure described below.

$R^7 =\!\!-\!\!C_{12}H_{25}$

This product was a brown transparent liquid.

<Synthesis of Glycerin Co-Modified Organopolysiloxane C>

First, 146.9 g of methylhydrogen polysiloxane represented by the average composition formula $MD_{33}D^H{}_3M$, 40.2 g of tris-trimethylsiloxy vinyl silane, 12.9 g of diglycerine monoallyl ether, and 12.9 g of isopropyl alcohol (IPA) were added into a reaction vessel and heated to 70° C. while stirring under a stream of nitrogen. Next, 0.100 g of a platinum catalyst was added, and the mixture was reacted for 10 hours. The completion of the reaction was confirmed by an alkali decomposition gas generation method. After the reaction solution was heated at 120° C. under reduced pressure to distill out the low-boiling components, the product was subjected to filtration to obtain a glycerin co-modified organopolysiloxane C having a siloxane dendron structure represented by the average composition formula $MD_{33}D^{R1}{}_2D^{R4}{}_1M$.

In this formula, $R^1$ and $R^4$ are synonymous with those described above.

This product was a light yellow viscous transparent liquid.

Formulation Example 1

Liquid Foundation (W/O)

Components

| | | |
|---|---|---|
| 1. | Decamethyl cyclopentasiloxane | 30 parts |
| 2. | Isotridecyl isononanoate | 3 parts |
| 3. | Glyceryl tricapryl-caprate | 2 parts |
| 4. | Polyether-modified silicone (*1) | 1.5 parts |
| 5. | Glycerin co-modified organopolysiloxane A | 0.5 parts |
| 6. | Organo-modified clay mineral (Bentone 38V) | 1.5 parts |
| 7. | Octyl methoxycinnamate | 5 parts |
| 8. | Silicone treated titanium oxide | 8.5 parts |
| 9. | Silicone-treated red iron oxide | 0.4 parts |
| 10. | Silicone-treated yellow iron oxide | 1 part |
| 11. | Silicone-treated black iron oxide | 0.1 parts |
| 12. | Decamethyl cyclopentasiloxane, dimethicone crosspolymer (*2) | 2 parts |
| 13. | Copolymer composition described in Practical Example 1 | 2 parts |
| 14. | 1,3-butylene glycol | 5 parts |
| 15. | Glycerin | 3 parts |
| 16. | Sodium chloride | 0.5 parts |
| 17. | Preservative | q.s. |
| 18. | Purified water | Remainder |
| 19. | Perfume | q.s. |

Note
(*1): ES-5300, manufactured by Dow Corning Toray Co., Ltd. was used.
Note
(*2): DC9040 manufactured by Dow Corning Corporation was used.

(Production Method)
Step 1: Components 1, 4, 6, 7, 12, and 13 were mixed while stirring.
Step 2: Components 2, 3, 5, and 8 to 11 were kneaded and mixed using a triple roller.
Step 3: The mixture of step 2 was added to the mixture obtained in step 1 while stirring, and the mixture was further mixed while stirring.
Step 4: An aqueous phase in which components 14 to 19 were dissolved uniformly was added to the mixture obtained in step 3 and emulsified, and a product was obtained by filling a container with this mixture.

The resulting W/O-type liquid foundation demonstrated excellent emulsion stability when used, excellent water resistance and cosmetic durability, excellent masking of skin imperfections and wrinkles, and excellent spread and adhesiveness.

Formulation Example 2

Liquid Foundation (W/O)

Components

| | | |
|---|---|---|
| 1. | Isododecane | 20 parts |
| 2. | Isohexadecane | 10 parts |
| 3. | Isotridecyl isononanoate | 3 parts |
| 4. | Glyceryl tricapryl-caprate | 2 parts |
| 5. | Polyether-modified silicone (*1) | 1.5 parts |
| 6. | Glycerin co-modified organopolysiloxane B | 0.5 parts |
| 7. | Organo-modified clay mineral (Bentone 38V) | 1.5 parts |
| 8. | Octyl methoxycinnamate | 5 parts |
| 9. | Octylsilane treated titanium oxide | 8.5 parts |
| 10. | Octylsilane treated red iron oxide | 0.4 parts |
| 11. | Octylsilane treated yellow iron oxide | 1 part |
| 12. | Octylsilane treated black iron oxide | 0.1 parts |
| 13. | Dimethicone-dimethicone crosspolymer (*2) | 2 parts |
| 14. | Copolymer composition described in Practical Example 2 | 1 part |
| 15. | Trimethylsiloxysilicate | 0.5 parts |
| 16. | 1,3-butylene glycol | 5 parts |
| 17. | Glycerin | 3 parts |
| 18. | Sodium chloride | 0.5 parts |
| 19. | Preservative | q.s. |
| 20. | Purified water | Remainder |
| 21. | Perfume | q.s. |

Note
(*1): ES-5300, manufactured by Dow Corning Toray Co., Ltd. was used.
Note
(*2): DC9045, manufactured by Dow Corning Corporation was used.

(Production Method)
Step 1: Components 1, 2, 5, 7, 8, 13, 14, and 15 were mixed while stirring.
Step 2: Components 3, 4, 6, and 9 to 12 were kneaded and mixed using a triple roller.
Step 3: The mixture of step 2 was added to the mixture obtained in step 1 while stirring, and the mixture was further mixed while stirring.

Step 4: An aqueous phase in which components 16 to 21 were dissolved uniformly was added to the mixture obtained in step 3 and emulsified, and a product was obtained by filling a container with this mixture.

The resulting W/O-type liquid foundation demonstrated excellent emulsion stability when used, excellent water resistance and cosmetic durability, excellent masking of skin imperfections and wrinkles, a light texture, and excellent adhesion.

Formulation Example 3

Liquid Foundation (O/W)

Components

| | | |
|---|---|---|
| 1. Carboxydecyl trisiloxane | 1 | part |
| 2. Polysorbate 80 | 1.2 | parts |
| 3. Sorbitan sesquioleate | 0.2 | parts |
| 4. Glyceryl stearate | 1.5 | parts |
| 5. Behenyl alcohol | 2.5 | parts |
| 6. Cyclopentasiloxane | 8 | parts |
| 7. Dimethicone (viscosity: 6 mPa · s) | 3 | parts |
| 8. Squalane | 3 | parts |
| 9. Isotridecyl isononanoate | 3 | parts |
| 10. Glyceryl tricapryl-caprate | 3 | parts |
| 11. Copolymer composition described in Practical Example 3 | 1 | part |
| 12. Glycerin co-modified organopolysiloxane B | 0.2 | parts |
| 13. Silicone treated titanium oxide | 8.5 | parts |
| 14. Silicone-treated red iron oxide | 0.4 | parts |
| 15. Silicone-treated yellow iron oxide | 1 | part |
| 16. Silicone-treated black iron oxide | 0.1 | parts |
| 17. 1,3-butylene glycol | 8 | parts |
| 18. Sodium hydroxide aqueous solution (1%) | 15 | parts |
| 19. Carbomer (2%) | 10 | parts |
| 20. Purified water | Remainder | |

(Production Method)
Step 1: Components 1 to 8 and 11 were mixed while heating and stirring.
Step 2: Components 9, 10, and 12 to 16 were kneaded and mixed using a triple roller.
Step 3: The mixture of step 2 was added to the mixture obtained in step 1 while stirring, and the mixture was further mixed while stirring.
Step 4: After an aqueous phase in which components 17, 18, and 20 were dissolved uniformly was added to the mixture obtained in step 3 and emulsified at 70° C., component 19 was added while stirring. The mixture was cooled, and a product was obtained by filling a container with this mixture.

The resulting W/O-type liquid foundation demonstrated excellent emulsion stability when used, excellent water resistance and cosmetic durability, excellent masking of skin imperfections and wrinkles, and excellent spread and adhesiveness.

Formulation Example 4

Sunscreen (W/O)

Components

| | | |
|---|---|---|
| 1. Dimethicone (viscosity: 6 mPa · s) | 3.8 | parts |
| 2. Cyclopentasiloxane | 6.7 | parts |
| 3. Isotridecyl isononanoate | 4 | parts |
| 4. Polyether-modified silicone (*1) | 2 | parts |
| 5. Cyclopentasiloxane, cross-linked polyether-modified silicone (*2) | 2.5 | parts |
| 6. Cyclopentasiloxane-dimethicone crosspolymer (*3) | 1.5 | parts |
| 7. Organomodified bentonite | 0.2 | Parts |
| 8. Silicone treated microparticle zinc oxide dispersion (zinc oxide: 60 wt %) (*4) | 35 | parts |
| 9. Silicone treated fine particulate titanium oxide dispersion (titanium oxide: 40 wt %) (*5) | 25 | parts |
| 10. Copolymer composition described in Practical Example 4 | 3.3 | parts |
| 11. 1,3-butylene glycol | 2 | parts |
| 12. Sodium citrate | 0.2 | Parts |
| 13. Sodium chloride | 0.5 | parts |
| 14. Purified water | Remainder | |

Note
(*1): ES-5300, manufactured by Dow Corning Toray Co., Ltd. was used.
Note
(*2): DC-9011, manufactured by Dow Corning Toray Co., Ltd. was used.
Note
(*3): DC-9040, manufactured by Dow Corning Toray Co., Ltd. was used.
Note
(*4): A slurry prepared by mixing 10 parts of glycerin co-modified organopolysiloxane B, 40 parts of a fine particulate titanium oxide (trade name: MTY-02, manufactured by Tayca Corporation, particle size: 10 nm), and 50 parts of decamethylpentasiloxane with zirconia beads and dispersing the mixture with a paint shaker was used.
Note
(*5): A slurry prepared by mixing 5 parts of glycerin co-modified organopolysiloxane B, 60 parts of a fine particulate zinc oxide (trade name: FIXEX-30S-LPT, manufactured by Sakai Chemical Industry Co., Ltd., particle size: 35 nm), and 35 parts of decamethylpentasiloxane were mixed with zirconia beads and dispersing the mixture with a paint shaker was used.

(Production Method)
Step 1: Components 1 to 10 were mixed.
Step 2: Components 11 to 14 were mixed.
Step 3: After an aqueous phase obtained in step 2 was added to the mixture obtained in step 1 while stirring and emulsified, a product was obtained by filling a container with the mixture.

The resulting sunscreen did not exhibit any separation of the oil components or powders, and it was possible to stock the sunscreen for a long period of time at approximately 40° C. (air temperature during the summer), demonstrating excellent stability over time. Further, the sunscreen had an excellent feel of use with good spread and reduced stickiness when used. The sunscreen was free of irritation and provided long-lasting ultraviolet light protection effects. No changes were observed in this good feel of use before and after being stored at approximately 40° C.

Formulation Example 5

Sunscreen (Shaking Type)

Components

| | | |
|---|---|---|
| 1. Octyl methoxycinnamate | 6 | parts |
| 2. Isotridecyl isononanoate | 7 | parts |
| 3. Polyether-modified silicone (*1) | 3 | parts |
| 4. Diethylamino hydroxybenzoyl hexyl benzoate | 2 | parts |
| 5. Titanium oxide slurry (*1) | 5 | parts |
| 6. Zinc oxide slurry (*2) | 28 | parts |
| 7. Cyclopentasiloxane | 18.2 | parts |
| 8. Dimethicone crosspolymer | 3 | parts |
| 9. Trimethylsiloxysilicate | 2 | parts |
| 10. Copolymer composition described in Practical Example 5 | 1 | part |
| 11. Preservative | 0.1 | parts |
| 12. Ethanol | 5 | parts |
| 13. 1,3-butylene glycol | 3 | parts |
| 14. Purified water | Remainder | |

Note
(*1): ES-5300, manufactured by Dow Corning Toray Co., Ltd. was used.
Note
(*2): The fine particulate titanium oxide slurry described in formulation example 4 was used.
Note
*3: The fine particulate zinc oxide slurry described in formulation example 4 was used.

(Production Method)
Step 1: Components 1 to 10 were mixed.
Step 2: A mixture of components 11 to 14 was added to the mixture of step 1 and emulsified.

When the resulting sunscreen was applied to the skin, the sunscreen demonstrated an excellent feel of use with reduced stickiness and provided a long-lasting ultraviolet light protection effect.

Formulation Example 6

Foundation Cream

Components

| | | |
|---|---|---|
| 1. | Dimethylpolysiloxane (viscosity: 2 mPa · s) | 2 parts |
| 2. | Decamethyl cyclopentasiloxane | 10 parts |
| 3. | Polyether-modified silicone (*1) | 2.5 parts |
| 4. | Cetyl isooctanoate | 5 parts |
| 5. | Glycerin co-modified organopolysiloxane C | 0.5 parts |
| 6. | Copolymer composition described in Practical Example 6 | 3 parts |
| 7. | 2-ethylhexyl paramethoxycinnamate | 2 parts |
| 8. | Silicone elastomer (*2) | 4 parts |
| 9. | Silicone treated titanium oxide | 6 parts |
| 10. | Silicone-treated red iron oxide | 0.3 parts |
| 11. | Silicone-treated yellow iron oxide | 0.7 parts |
| 12. | Silicone-treated black iron oxide | 0.07 parts |
| 13. | Organomodified bentonite | 0.5 parts |
| 14. | Barium sulfate | 2 parts |
| 15. | Talc | 1 part |
| 16. | Nylon powder | 3 parts |
| 17. | Preservative | q.s. |
| 18. | Xanthan gum | 0.1 parts |
| 19. | L-ascorbic acid magnesium phosphate ester | 0.3 parts |
| 20. | Purified water | Remainder |

Note
(*1): ES-5612, manufactured by Dow Corning Toray Co., Ltd., was used.
Note
(*2): 9045 Silicone Elastomer Blend, manufactured by Dow Corning Corporation, was used.

(Production Method)
Step 1: Components 1 to 16 were mixed and dispersed.
Step 2: Components 17 to 20 were mixed.
Step 3: The mixture obtained in step 2 was added to the mixture obtained in step 1 and emulsified at room temperature, and a product was obtained by filling a container with the mixture.

This foundation cream demonstrated good spread, and excellent cosmetic film uniformity and adhesion to the skin. Additionally, skin imperfections, wrinkles, and pores were hardly noticeable. Further, the foundation cream had a stable emulsified state.

Formulation Example 7

Rouge

Components

| | | |
|---|---|---|
| 1. | Triethylhexanoin | 10.0 parts |
| 2. | Cetyl ethylhexanoate | 17.0 parts |
| 3. | Sorbitan sesquiisostearate | 4.0 parts |
| 4. | Microcrystalline wax | 10.0 parts |
| 5. | Paraffin wax | 15.0 parts |
| 6. | Diisostearyl malate | 7.0 parts |
| 7. | Glyceryl triisostearate | 9.0 parts |
| 8. | Propylene glycol dicaprylate | 7.0 parts |
| 9. | Inulin stearate (product name: Rheopearl ISL2 manufactured by Chiba Flour Milling Co., Ltd.) | 2.0 parts |

-continued

| | | |
|---|---|---|
| 10. | Polyether-modified silicone (*1) | 3.0 parts |
| 11. | Copolymer composition described in Practical Example 7 | 3.0 parts |
| 12. | Dimethylpolysiloxane (viscosity: 100 mPa · s) solution of trimethylsiloxy silicic acid (active ingredient: 33%) | 2.0 parts |
| 13. | Yellow No. 4 | q.s. |
| 14. | Titanium oxide | 1.0 parts |
| 15. | Black iron oxide | 1.0 parts |
| 16. | Mica | 1.0 parts |
| 17. | Red 104 | q.s. |
| 18. | Purified water | 7.0 parts |
| 19. | 1,3-butylene glycol | 1.0 parts |
| 20. | Preservative | q.s. |
| 21. | Perfume | q.s. |

Note
(*1): ES-5612, manufactured by Dow Corning Toray Co., Ltd., was used.

(Production Method)
Step 1: Components 1 to 17 were heated and dissolved.
Step 2: Components 18 to 20 were mixed.
Step 3: The mixture obtained in step 2 was added to the mixture obtained in step 1 and further agitated and mixed.
Step 4: Component 21 was added to the mixture obtained in step 3, and a product was obtained by filling a container with the mixture.

The rouge had a luxurious feel and excellent spreadability; could be applied uniformly to the lips; and could deliver a finish having superior luster and feeling of sheerness. In addition, there was no sticky feel on the lips after application and the product had excellent storage stability.

Formulation Example 8

Liquid Rouge

Components

| | | |
|---|---|---|
| 1. | Copolymer composition described in Practical Example 9 | 5 parts |
| 2. | Cyclopentasiloxane/trimethylsiloxy silicic acid (*1) | 5 parts |
| 3. | Phenyl methyl silicone | 10 parts |
| 4. | Ethylhexyl palmitate | 10 parts |
| 5. | Mist-like silicic anhydride | 0.1 parts |
| 6. | Spherical urethane powder | 5 parts |
| 7. | Polyether-modified silicone (*2) | 5 parts |
| 8. | Octylmethoxycinnamate | 1 part |
| 9. | Red No. 202 | 0.5 parts |
| 10. | Titanium oxide | 0.5 parts |
| 11. | Titanated mica | 3 parts |
| 12. | Perfume | 0.1 parts |
| 13. | Ethanol | 10 parts |
| 14. | Preservative | 0.2 Parts |
| 15. | Sodium chloride | 0.1 parts |
| 16. | Purified water | Remainder |

Note
(*1): BY11-018, manufactured by Dow Corning Toray Co., Ltd., was used.
Note
(*2): BY11-030, manufactured by Dow Corning Toray Co., Ltd., was used.

(Production Method)
A: Components 1 to 11 were dispersed and mixed.
B: Separately, components 12 to 16 were dissolved uniformly.
C: B was added to A and emulsified. After the mixture was defoamed, a water-in-oil emulsion lipstick was obtained by filling a container with the mixture.

Formulation Example 9

Lipstick

Components

| | | |
|---|---|---|
| 1. | Polyethylene-polypropylene copolymer | 5 parts |
| 2. | Candelilla wax | 5 parts |
| 3. | Carnauba wax | 4.5 parts |
| 4. | Copolymer composition described in Practical Example 8 | 0.5 parts |
| 5. | Petrolatum | 10 parts |
| 6. | Cetyl 2-ethylhexanoate | 10 parts |
| 7. | Diglycerin diisostearate | 14.5 parts |
| 8. | Macadamia nut oil | 7 parts |
| 9. | Inulin stearate (product name: Rheopearl ISK2 manufactured by Chiba Flour Milling Co., Ltd.) | 23 parts |
| 10. | Polyether-modified oil (*1) | 2 parts |
| 11. | Red No. 201 | 1 part |
| 12. | Red No. 202 | 3 parts |
| 13. | Yellow No. 4 aluminum lake | 3 parts |
| 14. | Titanium oxide | 1 part |
| 15. | Black iron oxide | 0.5 parts |
| 16. | Iron oxide-coated titanated mica | 10 parts |
| 17. | Preservative | q.s. |
| 18. | Perfume | q.s. |

Note
(*1): ES-5300, manufactured by Dow Corning Toray Co., Ltd., was used.

(Production Method)
A: Components 1 to 9 were heated and dissolved. Then, components 10 to 16 were added and mixed uniformly.
B: Components 17 and 18 were added to A, and a lipstick was obtained by filling a container with the mixture.

Formulation Example 10

Lip Gloss

Components

| | | |
|---|---|---|
| 1. | Polyamide-modified silicone (*1) | 10 parts |
| 2. | Glycerin co-modified organopolysiloxane C | 1 part |
| 3. | Copolymer composition described in Practical Example 1 | 1 part |
| 4. | Methyl phenyl-modified silicone | 27 parts |
| 5. | Isodecyl isononanoate | 38 parts |
| 6. | Isohexadecane | 14 parts |
| 7. | Trioctanoin | 2 parts |
| 8. | Titanated mica | 3 parts |

Note
(*1): 2-8178 Gellant, manufactured by Dow Corning Corporation, was used.

(Production Method)
After the respective components were heated and mixed at 100° C., a product was obtained by filling a container with the mixture.

This lip gloss yielded good oil-based raw material adaptability and good storage stability when the product was stocked.

Formulation Example 11

Eye Shadow

Components

| | | |
|---|---|---|
| 1. | Dimethylpolysiloxane (viscosity: 2 mPa·s) | 13 parts |
| 2. | Dimethylpolysiloxane (viscosity: 6 mPa·s) | 11 parts |
| 3. | Polyether-modified silicone (*1) | 2 parts |
| 4. | PEG (10) lauryl ether | 0.5 parts |
| 5. | Copolymer composition described in Practical Example 3 | 1 part |
| 6. | Octylsilane treated titanium oxide | 6.2 parts |
| 7. | Octylsilane-treated sericite | 4 parts |
| 8. | Octylsilane-treated mica | 6 parts |
| 9. | Sodium chloride | 2 parts |
| 10. | Propylene glycol | 8 parts |
| 11. | Preservative | q.s. |
| 12. | Perfume | q.s. |
| 13. | Purified water | Remainder |

Note
(*1): ES-5612, manufactured by Dow Corning Toray Co., Ltd., was used.

(Production Method)
A: Components 1 to 4 were mixed, and components 5 to 8 were then added and dispersed uniformly.
B: Components 9 to 13 were dissolved uniformly.
C: B was gradually added to A and emulsified while stirring to obtain an eye shadow.

The resulting eye shadow demonstrated smooth spread and excellent color when used.

Formulation Example 12

Mascara

Components

| | | |
|---|---|---|
| 1. | Paraffin wax | 5 parts |
| 2. | Light liquid isoparaffin | Remainder |
| 3. | Capryl methicone | 0.5 parts |
| 4. | Polyether-modified silicone (*1) | 0.5 parts |
| 5. | Copolymer composition described in Practical Example 2 | 0.5 parts |
| 6. | Trioctanoin | 13 parts |
| 7. | Decamethyl cyclopentasiloxane | 14.5 parts |
| 8. | Inulin stearate | 5 parts |
| 9. | Cyclopentasiloxane-dimethicone crosspolymer (*2) | 10 parts |
| 10. | Fluorine compound surface-treated black iron oxide | 6 parts |
| 11. | Sucrose fatty acid ester | 4 parts |
| 12. | Beeswax | 5 parts |
| 13. | Pentaerythrityl rosinate | 5 parts |
| 14. | Preservative | q.s. |
| 15. | Purified water | 5 parts |

Note
(*1): ES-5300, manufactured by Dow Corning Toray Co., Ltd., was used.
Note
(*2): DC-9040, manufactured by Dow Corning Corporation, was used.

(Production Method)
After components 1 to 13 were dissolved while heating, the components were sufficiently mixed and dispersed. A mixture of components 14 and 15 was added to this mixture and emulsified, and a product was obtained by filling a container with the mixture.

The resulting mascara had a deep dark appearance and excellent sheen when used. In addition, the mascara demonstrated good adhesion to the eyelashes and an excellent eyelash curl volume effect which lasted a long time.

Formulation Example 13

Powder Foundation

Components

| | | |
|---|---|---|
| 1. | Talc | Remainder |
| 2. | Mica | 3.0 parts |

| | |
|---|---|
| 3. Dimethicone/vinyldimethicone crosspolymer/silica | 1.0 parts |
| 4. Silicone treated titanium oxide | 9.0 parts |
| 5. Silicone-treated fine particulate zinc oxide | 5.0 parts |
| 6. Silicone-treated fine particulate titanium oxide | 5.0 parts |
| 7. Red iron oxide | 0.2 parts |
| 8. Yellow iron oxide | 1.4 parts |
| 9. Black iron oxide | 0.3 parts |
| 10. Plate-like barium sulfate (average particle diameter: 30 μm) | 7.5 parts |
| 11. Polymethyl methacrylate | 7.5 parts |
| 12. Preservative | 0.2 Parts |
| 13. Phenyl methyl silicone | 5.0 parts |
| 14. Copolymer composition described in Practical Example 8 | 2.0 parts |
| 15. Ethylhexyl methoxycinnamate | 1.0 parts |
| 16. Diisostearyl malate | 3.0 parts |
| 17. Dimethylpolysiloxane (350 cSt) | 2.0 parts |
| 18. Glycerin | 0.2 Parts |
| 19. Perfume | q.s. |

1. Components 11 to 18 are mixed and dissolved.
2. Components 1 to 10 are mixed.
3. The mixture obtained in step 2 is added to the mixture obtained in step 1. The resulting mixture is mixed, kneaded, and pulverized.
4. The pulverized product obtained in step 3 is press-molded with a metal mold to obtain a solid powder foundation.

The resulting powder foundation demonstrated good cosmetic durability and excellent spread when used.

The invention claimed is:

1. A copolymer composition comprising:
a copolymer comprising:
(A) an unsaturated monomer having a carbosiloxane dendrimer structure represented by the following formula (A-1):

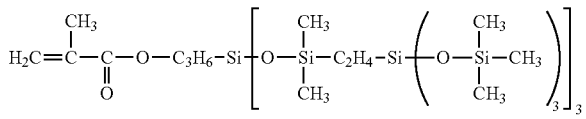

(B) at least one type of unsaturated monomer selected from the group consisting of methyl methacrylate, n-butyl acrylate, and 2-ethylhexyl acrylate;
wherein the copolymer comprises a mass ratio range satisfying a relation in which [mass of component (A)/mass of all monomers]:[mass of component (B)/mass of all monomers] is [0.45 to 0.5]:[0.55 to 0.5]; and
wherein the copolymer comprises a calculated glass transition point (Tg) of from 49 to 61 degrees Celsius; and
(C) an oil agent comprising (C1) a hydrophobic silicone oil having a viscosity of from 0.65 to 100,000 mm$^2$/s at 25° C.

2. A cosmetic raw material comprising the copolymer composition according to claim 1.

3. A cosmetic comprising the copolymer composition according to claim 1.

4. The cosmetic according to claim 3, further comprising at least one type selected from the group consisting of (D) a powder or colorant, (E) a surfactant, (F) an oil-soluble gelling agent, (G) an organically modified clay mineral, (H) a silicone resin, (I) a silicone rubber, (J) a silicone elastomer, (K) an organically modified silicone, (L) an ultraviolet ray protective component, and (M) a water-soluble polymer.

5. The cosmetic according to claim 3, further defined as a skin care product, a hair product, an antiperspirant product, a deodorant product, a makeup product, or an ultraviolet ray protective product.

6. The copolymer composition according to claim 1, wherein (C) the oil agent further comprises an oil selected from a group consisting of hydrocarbon oils, fatty acid ester oils, and combinations thereof.

7. The cosmetic according to claim 4, wherein (C) the oil agent further comprises an oil selected from a group consisting of hydrocarbon oils, fatty acid ester oils, and combinations thereof.

8. The copolymer composition according to claim 1, wherein (C) the oil agent is (C1) the hydrophobic silicone oil having a viscosity of from 0.65 to 100,000 mm$^2$/s at 25° C.

9. The copolymer composition according to claim 1, wherein (C1) the hydrophobic silicone oil is decamethyl cyclopentasiloxane (D5) or dimethylpolysiloxane having a viscosity of 2 mPa·s.

10. The cosmetic according to claim 3, wherein (C1) the hydrophobic silicone oil is decamethyl cyclopentasiloxane (D5) or dimethylpolysiloxane having a viscosity of 2 mPa·s.

11. The copolymer composition according to claim 1, wherein component (B) comprises methyl methacrylate and n-butyl acrylate.

12. The copolymer composition according to claim 11, wherein component (B) consists of methyl methacrylate and n-butyl acrylate.

13. The copolymer composition according to claim 11, wherein the methyl methacrylate is present in component (B) in an amount greater than the n-butyl acrylate.

14. The copolymer composition according to claim 1, wherein component (B) comprises methyl methacrylate and 2-ethylhexyl acrylate.

15. The copolymer composition according to claim 14, wherein component (B) consists of methyl methacrylate and 2-ethylhexyl acrylate.

16. The copolymer composition according to claim 14, wherein the methyl methacrylate is present in component (B) in an amount greater than the 2-ethylhexyl acrylate.

17. The copolymer composition according to claim 1, wherein the mass ratio range is 0.45:0.55.

18. The copolymer composition according to claim 1, wherein the mass ratio range is 0.5:0.5.

19. The copolymer composition according to claim 1, wherein the copolymer is free of an unsaturated monomer having a long-chain alkyl group with 14 to 22 carbon atoms.

20. The copolymer composition according to claim 1, wherein the copolymer consists of components (A) and (B).

* * * * *